(12) United States Patent
Stansbury et al.

(10) Patent No.: US 6,184,339 B1
(45) Date of Patent: Feb. 6, 2001

(54) HIGH STRENGTH POLYMERIC NETWORKS DERIVED FROM (METH) ACRYLATE RESINS WITH ORGANOFLUORINE CONTENT AND PROCESS FOR PREPARING SAME

(75) Inventors: Jeffrey W. Stansbury, Frederick; Joseph M. Antonucci, Kensington; Kyung M. Choi, Gaithersburg, all of MD (US)

(73) Assignee: The United States of America as represented by the Secretary of the Commerce, Washington, DC (US)

( * ) Notice: Under 35 U.S.C. 154(b), the term of this patent shall be extended for 0 days.

(21) Appl. No.: 08/967,896

(22) Filed: Nov. 12, 1997

Related U.S. Application Data

(60) Provisional application No. 60/030,911, filed on Nov. 14, 1996.

(51) Int. Cl.[7] .................................. C08F 2/48; C08J 6/08; C08K 2/00; C08G 65/00
(52) U.S. Cl. ........................... 528/407; 522/90; 522/155; 522/156; 522/100; 522/908; 523/109; 523/116; 523/118; 523/115; 523/300; 423/226; 528/406; 528/418; 528/59; 528/65; 528/87
(58) Field of Search .............................. 528/407, 59, 65, 528/418, 87, 406; 522/90, 96, 100, 155, 156; 523/109; 433/226, 228.1

(56) References Cited

U.S. PATENT DOCUMENTS

| | | |
|---|---|---|
| 3,852,222 * | 12/1974 | Field et al. ............................ 525/528 |
| 3,872,045 * | 3/1975 | Field et al. ............................ 523/435 |
| 3,879,430 * | 4/1975 | O'Rear et al. ....................... 549/559 |
| 4,356,296 | 10/1982 | Griffith et al. . |
| 4,396,377 | 8/1983 | Roemer et al. . |
| 4,396,476 | 8/1983 | Roemer et al. . |
| 4,514,342 | 4/1985 | Billington et al. . |
| 4,525,493 | 6/1985 | Omura et al. . |
| 4,536,523 | 8/1985 | Antonucci . |
| 4,539,382 | 9/1985 | Omura et al. . |
| 4,616,073 * | 10/1986 | Antonucci ............................ 526/246 |
| 4,650,847 | 3/1987 | Omura et al. . |
| 4,871,786 | 10/1989 | Aasen et al. . |
| 4,914,171 * | 4/1990 | Zweig ................................... 526/246 |
| 5,004,790 * | 4/1991 | Harnish et al. ...................... 526/242 |
| 5,061,184 | 10/1991 | Yamazaki et al. . |
| 5,075,378 * | 12/1991 | Smierciak et al. ................... 525/109 |
| 5,380,901 | 1/1995 | Antonucci et al. . |
| 5,406,641 | 4/1995 | Bigley, Jr. et al. . |
| 5,485,541 | 1/1996 | Bigley, Jr. et al. . |
| 5,486,548 | 1/1996 | Podszun et al. . |

FOREIGN PATENT DOCUMENTS 1199937    8/1989    (JP) .

OTHER PUBLICATIONS

Stansbury et al Polymer Preprints, 39(2), 878–879, 1998.*
Choi et al Chem. Mater. 1996, 8, 2704–2707.*
Antonucci et al. Polymer Preprints, 1993, 34, 403–404.*
Stansbury et al, Polymer Preprints, 1995, 36(1), 831–832.*
Stansbury et al, Polymer Preprints, 1997, 38(2), 96–97.*
Stansbury, Macromolecules, 1991, 24, 2029–2035.*
Antonucci et al, Polymer Preprints, 1990, 31, 320–321.*
T. Maruno et al, Synthesis and properties of fluorine–containing epoxy(meth)acrylate resins. *J. Polym. Sci.; Polym. Chem.* 1994, 32, 3211.
O. Nuyken et al, Studies on new non–shrinking, thermally stable Araldite–type photopolymers with pendent aryl acryloyl groups. *Angew. Makromol. Chem.* 1992, 199, 149.
J.M. Antonucci, J.W. Stansbury, S. Venz, Synthesis and properties of a polyfluorinated prepolymer multifunctional urethane methacrylate. In:*Progress in Biomedical Polymers*, C.G. Gebelein and R.L. Dunn, eds., Plenum Press, New York, 1990.

* cited by examiner

*Primary Examiner*—James J. Seidleck
*Assistant Examiner*—Sanza L. McClendon
(74) *Attorney, Agent, or Firm*—Stevens, Davis, Miller & Mosher, LLP

(57) ABSTRACT

Disclosed are fluorinated materials for use in dental uses and non-dental uses, e.g., adhesives or coatings. Multifunctional monomers and prepolymers with pendant (meth)acrylate groups were prepared from epoxide ring-opening reactions. Resins based on the fluorinated monomers and prepolymers with diluent comonomers, were photocured as composites with particulate fillers. Fluorine contents of the prepolymers ranged from 15 to 65%. Composites with high transverse strength (up to 120 MPa), low water sorption (as low as 0.11 mass %) and extremely low polymerization shrinkage (as low as 3.4% by volume) were obtained. The fluorinated resins may be employed to produce hydrophobic dental composite materials with high strength and low polymerization shrinkage.

17 Claims, 7 Drawing Sheets

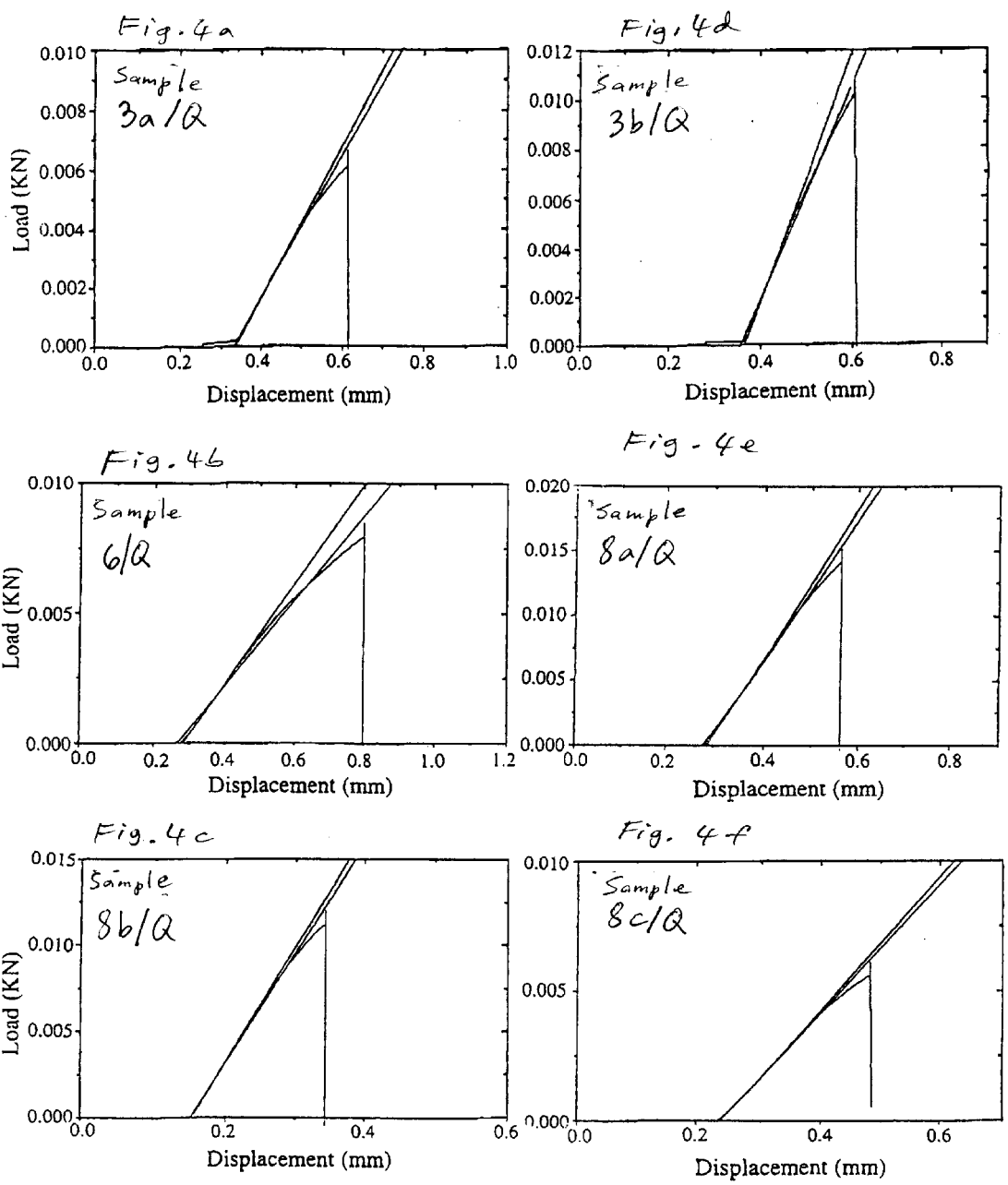

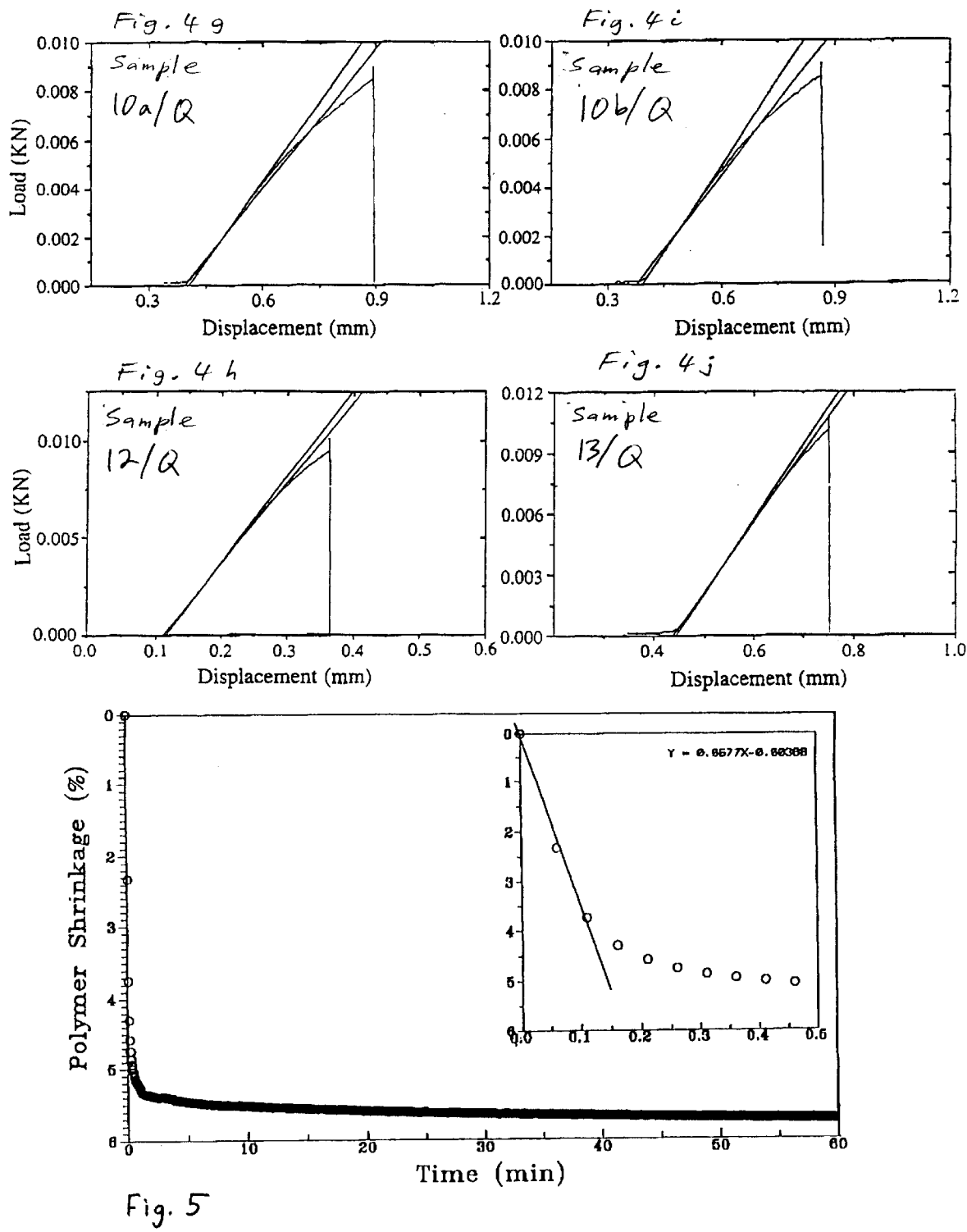

HIGH STRENGTH POLYMERIC NETWORKS DERIVED FROM (METH) ACRYLATE RESINS WITH ORGANOFLUORINE CONTENT AND PROCESS FOR PREPARING SAME

The present application claims priority of U.S. Provisional Patent Application Ser. No. 60/030,911, filed Nov. 14, 1996 and incorporated herein by reference.

FIELD OF THE INVENTION

The present invention relates to high strength polymeric networks derived from (meth)acrylate resins with moderate to high organofluorine contents and processes for making same. In particular, these resins are useful for dental composites.

BACKGROUND OF THE INVENTION

In dentistry, fluoropolymers have been widely utilized as components of medical devices because of the advantageous blend of chemical inertness with generally good biocompatibility. As the demand for advanced fluoropolymers with specific physical properties has grown, the molecular design of new types of fluorinated monomers has become an important area in synthetic polymer chemistry. Several properties of fluoropolymers, including their chemical inertness, hydrophobicity and toughness, make fluoropolymers interesting candidates for use in dental composites. However, due to low cohesive energies, amorphous fluorinated polymers tend to have unacceptably low mechanical strength.

In the area of aesthetic dental composite materials used for restorative and cosmetic purposes, the critical advancement in polymer technology was the introduction of 2,2-bis[p-(2'-hydroxy-3'-methacrylpropoxy)phenyl]propane, commonly referred to as Bis-GMA. This bulky dimethacrylate monomer is used with a low viscosity diluent comonomer, typically triethylene glycol dimethacrylate (TEGDMA), to prepare resins that form strong, densely cross-linked polymeric networks. More than 30 years after their introduction, resins based on varying proportions of Bis-GMA/TEGDMA still constitute the majority of commercial dental composite filling materials. Among other methacrylates utilized in commercial composite restoratives are urethane-containing monomers, such as urethane dimethacrylate (UDMA), and oligomers, such as the linear poly(urethane) prepared from Bis-GMA and hexamethylene diisocyanate (Bis-GMA-HMDI). Additional components of dental composites include a particulate filler, generally a barium, strontium or zirconium-containing glass and/or a microfine silica, whose surface is modified by attachment of a layer of a methacrylate-functionalized silane coupling agent, 3-methacryloxypropyltrimethoxysilane. A visible light activated photoinitiator system, camphorquinone (CQ) and an amine photoreductant, such as ethyl 4-N,N-dimethylaminobenzoate (EDMAB), allows the onset of polymerization to be controlled and then the rapid development of the cross-linked resin matrix to yield the cured composite under ambient conditions.

The relatively high modulus fillers used in dental composites serve to increase the strength, wear resistance and toughness of the resin matrix by reinforcement. The silane coupling agent plays a critical role in the development and maintenance of the reinforcing effect of the filler. Addition of substantial amounts of filler also minimizes the overall polymerization shrinkage associated with the continuous matrix phase. The particulate filler is also responsible for the translucence of the cured composite that gives it the natural tooth-like appearance. Coloration incorporated during the preparation of the filler can reproduce a broad spectrum of natural tooth shades and this allows near perfect matching of the composite to the adjacent tooth structure. The small particle size of the fillers used in the dental composites means that the composites can be polished to produce an excellent texture match with natural tooth.

Typical conventional resins based on Bis-GMA and TEGDMA ranging from mass ratios of 50:50 to 80:20, depending on the particular dental application, provide strong polymers. The cross-linked polymers are glasses whose degree of conversion of the available methacrylate groups is restricted by vitrification as the glass transition temperature of the developing polymer reaches the cure temperature. The degree of conversion attained during ambient temperature photopolymerzation is generally in the range 60% to 70%. The conversion varies somewhat with the intensity of the curing light; a more intense irradiation results in a faster polymerization with a greater exotherm. The fully cured resin is characterized as a highly cross-linked three dimensional polymeric network with many pendant methacrylate-terminated chains that lack sufficient mobility for further reaction.

Polymers designed to permanently replace tissues in the human body lost to disease, trauma or simple deterioration must satisfy a number of criteria. Beyond the obvious requirement of biocompatibility, long-tem stability dictates the need for materials that are highly resistant to alteration or degradation upon exposure to aqueous environments and resistant to a variety of chemical substances. In materials under consideration for dental composite restorative applications, the need for inert polymer matrices is coupled with the need for polymers that have adequate mechanical properties to minimize wear and fracture in both load-bearing and non-loadbearing situations. With an essentially limitless range of potential monomeric components available, advanced polymeric materials can be tailored to meet specific challenges such as these. Because of the excellent resistance displayed by fluoropolymers used in aqueous or other aggressive chemical environments, a variety of partially fluorinated monomers have been investigated previously as a means to achieve hydrophobic, chemically stable dental polymers. However, the use of significant proportions of fluorinated mono- or di-methacrylate monomers in dental resins typically produces polymers with unacceptably low mechanical strength properties primarily due to the low cohesive energies of amorphous fluorinated polymers.

Fluorinated resins for use in dental materials and a variety of other uses are disclosed by U.S. Pat. No. 4,616,073 (Antonucci); U.S. Pat. No. 4,914,171 (Zweig); and U.S. Pat. No. 5,380,901 (Antonucci et al.) all of which are incorporated herein by reference in their entirety. Fluorinated resins for use in dental materials and a variety of other uses are also disclosed by publications such as Douglas et al., *J. Dent. Res.* 58, 1981 (1979); Kurata et al., *J. Dent. Res.* 68, 481 (1989); Maruno et al., *J. Polym. Sci. Part A: Polym. Chem.* 32, 3211 (1994); Cassidy et al., *Eur. Polym. J.* 31, 353 (1995); and Stansbury et al., *Amer. Chem. Soc., Polym. Prepr.* 36(1), 831 (1995) all of which are incorporated herein by reference in their entirety.

Fluorinated polymers with moderate fluorine contents are generally hydrophobic but lack good mechanical strength properties due to the low cohesive energies associated with fluorine-substituted amorphous polymers. A photocurable dimethacrylate monomer 2,2-bis(p-(2'-hydroxy-3'- methacryloxy-propoxy)phenylene) propane (Bis-GMA) has been synthesized from the diglycidyl ether of bisphenol A and methacrylic acid. This reaction is shown by Reaction I.

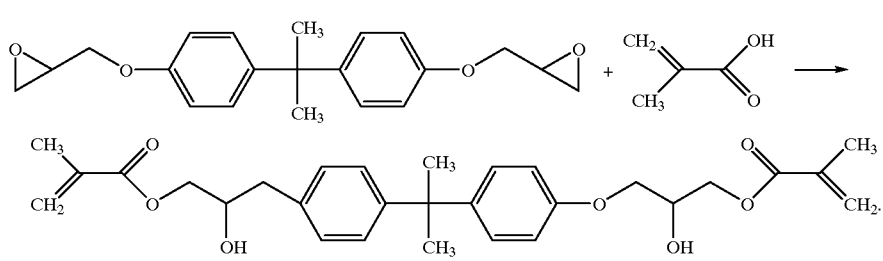

I

Bis-GMA has been used extensively as the basis of dental composite filling materials as disclosed by Bowen, R. L., U.S. Pat. No. 3,066,112; Bowen, R. L., U.S. Pat. No. 3,194,783; Venhoven, B. A. M., DeGee, A. J., Davidson, C. L., *Biomaterials* 1993, 14(11), 871; Stansbury, J. W., Antonucci, J. M., *Dent. Mater.* 1992, 8, 270; Venz, S.; Dickens, B., *J. Biomed. Mater. Res.* 1991,25,1231; Antonucci, J. M., Scott, G. L., *Polym. Prepr.,* 1995, 36 (1), 831; and Dulik, D., Bernier, R., Brauer, G. M., *J. Dent. Res.,* 1981, 60 (6), 983. The photopolymerization of an unfilled resin based on Bis-GMA diluted with triethylene glycol dimethylacrylate (TEGDMA) (7:3 by mass) produced a volumetric shrinkage of 7.9%. The resulting crosslinked polymer has a diametral tensile strength (DTS) and transverse strength (TS) of 42.2±3.6 MPa and 75.3±4.3 MPa, respectively and a water uptake of 3.8% as disclosed by Venhoven, B. A. M., DeGee, A. J., Davidson, C. L., *Biomaterials* 1993, 14(11), 871; Stansbury, J. W., Antonucci, J. M., *Dent. Mater.* 1992, 8, 270; and Venz, S., Dickens, B. *J. Biomed. Mater. Res.* 1991, 25, 1231.

However, new fluorocompounds are needed to improve the performance and durability of polymers used in challenging environments, such as in biocompatible materials for medical applications in the body. In dentistry, the requirements for durable fluoropolymers as cavity filling materials include high hydrophobicity, chemical and physical resistance, mechanical strength and resilience along with low surface energy, polymerization shrinkage, toxicity, and abrasion. It would be desirable to provide dental composite restoratives which are less prone to excessive polymerization shrinkage, water sorption, staining and brittle failure.

SUMMARY OF THE INVENTION

An object of the present invention is to provide (meth)acrylate resins with moderate to high organofluorine contents which are curable to form high strength polymeric networks.

Another object of the present invention is to provide an inert dental composite that has low shrinkage and significantly improved durability compared with existing dental materials.

Another object of the present invention is to provide a process for producing the inert dental composite that has low shrinkage and significantly improved durability compared with existing materials.

Another object of the present invention is to provide a method of using the inert dental composite that has low shrinkage and significantly improved durability compared with existing materials.

The introduction of covalently bound organofluorine into dental resins offers a technique to dramatically reduce water uptake, eliminate discoloration and improve the fracture toughness of composites. Through appropriate design of the fluoromonomers, materials achieving both low polymerization shrinkage and excellent mechanical strength are attained.

The initial objective of this investigation which resulted in the present invention was the development of practical synthetic routes to a variety of methacrylate monomers and reactive oligomers with moderate to high organofluorine contents. Photopolymerizable dental resins that combine the desirable properties of hydrophobicity, good mechanical strength and low polymerization shrinkage are sought for dental restorative applications. The oral environment provides significant challenges for the survival of polymeric materials. Dental restoratives experience continuous exposure to moisture, cyclic stresses and contact with a broad range of chemicals introduced through food and drink. It is predicted that resins based on these new fluorinated monomers will produce more inert, stain-resistant dental composite materials with improved long-term durability compared with existing hydrocarbon based resins. To aid in the selection of candidate fluorinated materials with potential for use in dental composites, the refractive index, water contact angle, water sorption, flexural strength and polymerization shrinkage of the photo-cured fluorinated resins and their composites were evaluated. Although not measured here, improvements in the fracture toughness of dental composites might also be expected for materials based on certain fluorinated resins. Due to the combination of low refractive indices, dielectric constants and surface free energies associated with polymers with moderate to high organofluorine contents, the readily polymerizable fluorinated monomers and oligomers developed here also could be considered for a variety of nonbiomaterial applications including structural and optical adhesives, chemically resistant coatings, fiber optics, electronics and integrated circuits.

The polymerizable fluorinated acrylate and methacrylate monomers and prepolymers of the present invention contain moderate to high fluorine contents (15 to 65% by mass). The monomers and prepolymers are designed to yield high strength, crosslinked polymers with low surface energies, low water sorption and low polymerization shrinkage. The high strength properties available from the polymers of these monomers and prepolymers are related to structural details incorporated in the monomers and prepolymers which include: details to increase the crosslink density in polymers, rigid backbones to enhance stiffness, and hydrogen bonding via urethane (or other) linkages to reinforce the polymeric network. These structural aspects can be employed separately or combined for greater effect. The potential exists to use liquid crystalline side-chains to further enhance strength of these materials.

The design of fluorinated monomers and prepolymers capable of rapid efficient polymerization to yield inert, crosslinked polymeric networks offers a means to avoid the processing problems encountered with thermoplastic fluoropolymers.

The present invention provides new families of fluoromonomers and fluoroprepolymers designed to improve the performance of aesthetic dental polymeric restorative materials. The present invention includes several types of moderately to highly fluorinated methacrylate-based monomers and prepolymers. The monomers and prepolymers are useful to prepare new fluoropolymers which exhibit excellent hydrophobicity and physical strength. In principle, these properties are inversely related; the physical strength of polymers rich in fluorine is generally reduced with increasing of fluorine content due to the low cohesive energy associated with fluoropolymers.

The fluorinated polymers are optically clear and have good solvent resistance, thermal stability, low dielectric constants and low refractive indices. Uses include: dental resins and composites, adhesives, protective coatings, optical devices and coatings, and electronic devices.

The present invention includes a synthesis process to achieve the specific objectives of developing high strength, hydrophobic crosslinked fluoropolymers, which efficiently form with low degrees of polymerization shrinkage. In its process respects, the present invention includes a process for preparing fluorinated monomers and prepolymers useful to make fluorinated dental composites based on high strength polymeric networks.

BRIEF DESCRIPTION OF THE DRAWINGS

FIGS. 4a–4j are plots of transverse strength of fluorinated dental composites based on prepolymer samples.

FIG. 5 plots polymer shrinkage versus time.

DETAILED DESCRIPTION OF THE PREFERRED EMBODIMENTS

Figure 1:
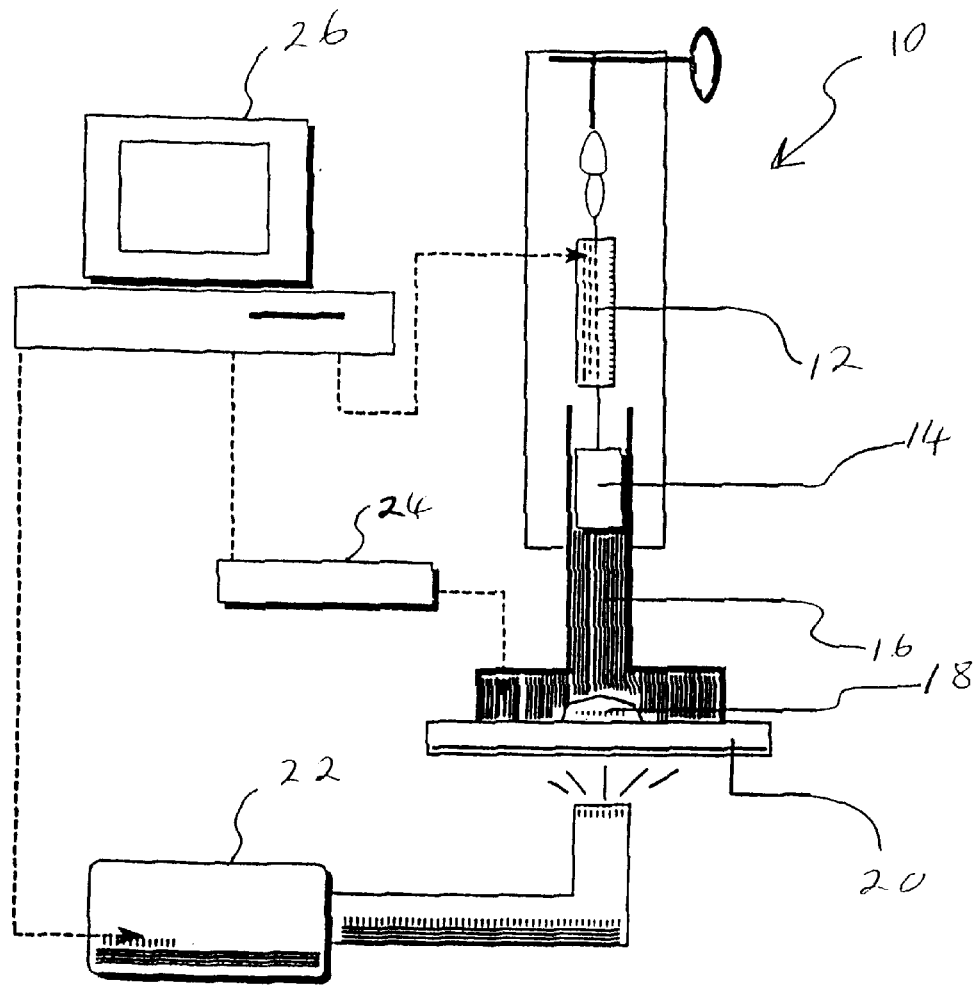
FIG. 1 is a diagram of a mercury dilatometer for measurement of polymerization shrinkage of activated resin, activated resins were placed on a quartz plate and photocured using a visible light.
Figure 2A:
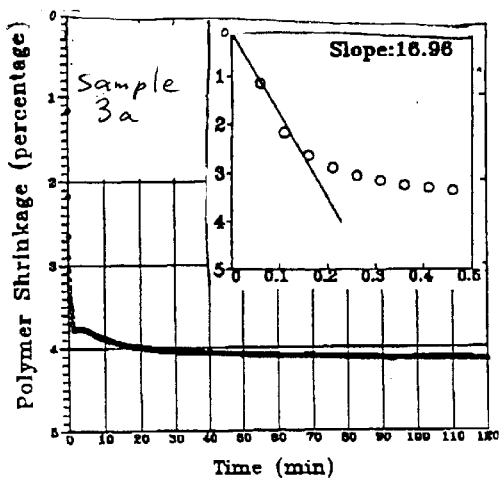
FIGS. 2a–2j are plots of polymerization shrinkage of activated resins based on highly fluorinated multifunctional oligomers by photocuring prepolymer samples.
Figure 2D:
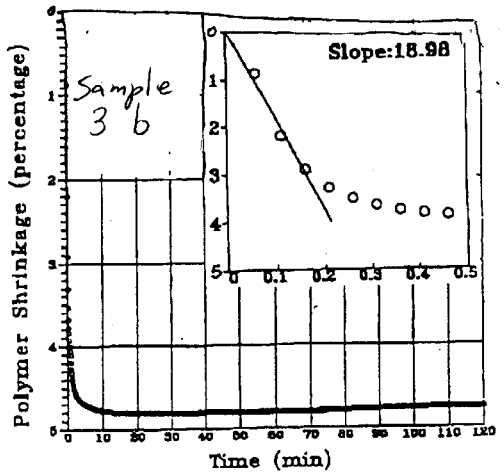
Figure 2B:
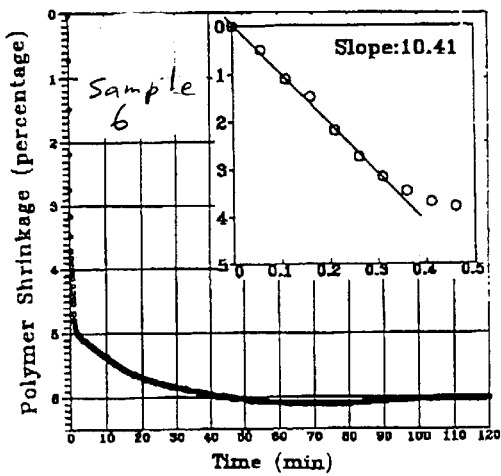
Figure 2E:
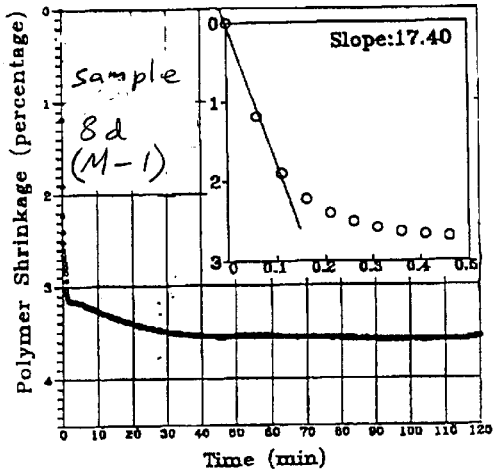
Figure 2C:
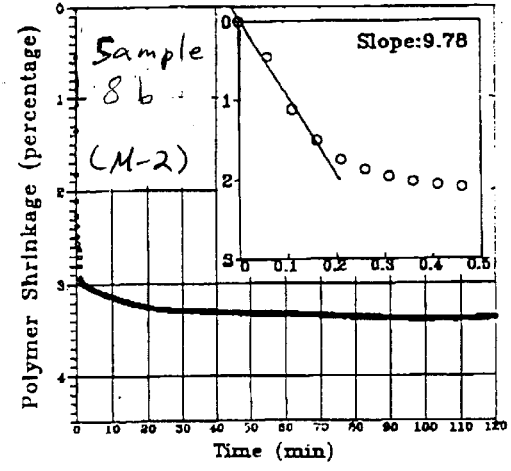
Figure 2F:
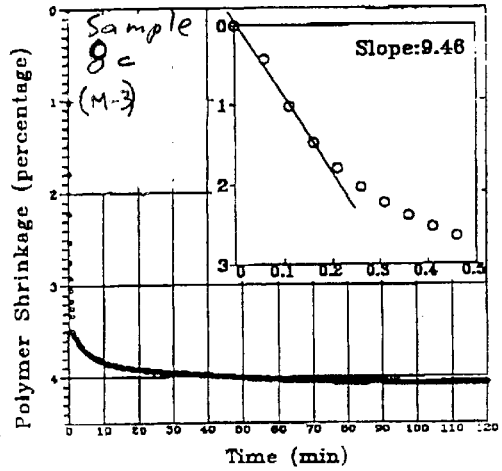
Figure 2G:
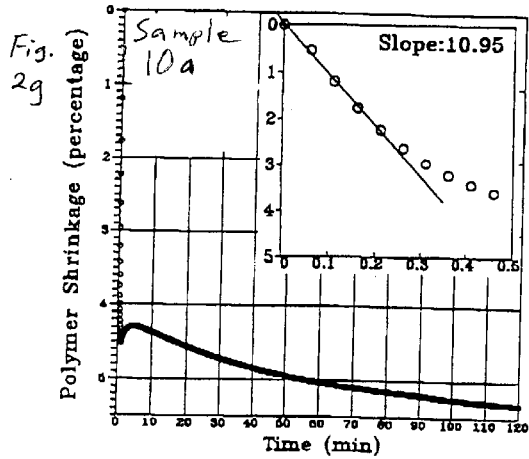
Figure 2I:
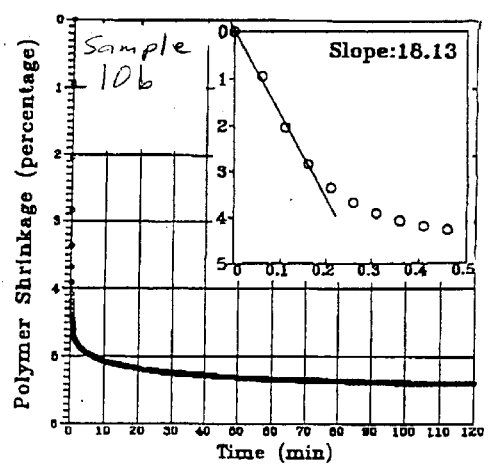
Figure 2H:
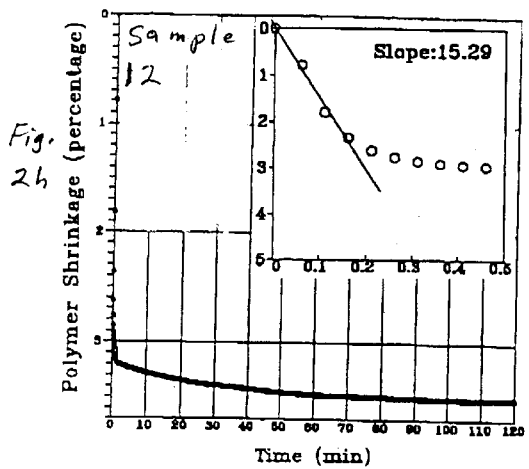
Figure 2J:
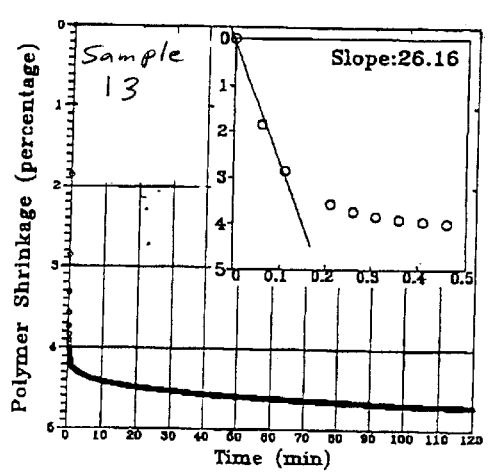

The present invention provides (meth)acrylate resins with moderate to high organofluorine contents which are curable to form high strength polymeric networks. The resins are made from moieties, having the following structural Formula II, IIIa, IIIb, IIIc, IIId and/or IV:

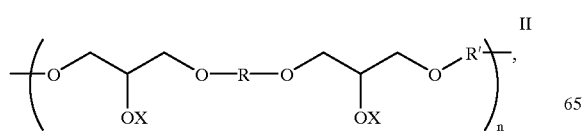

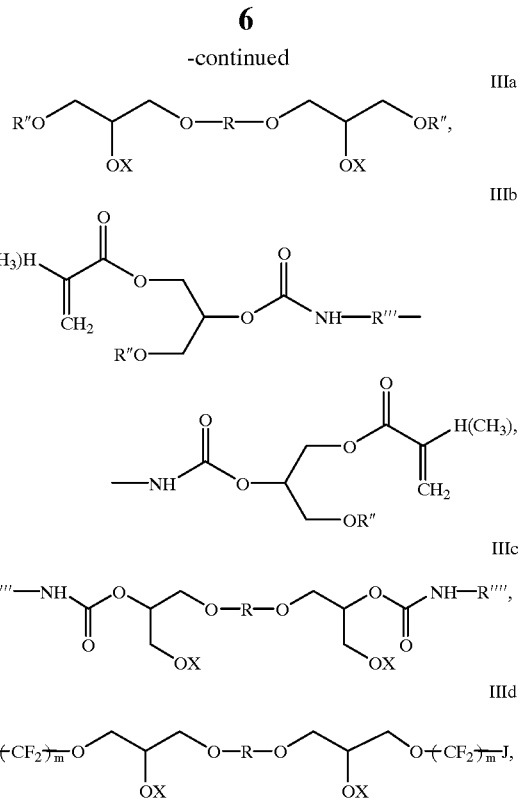

wherein J is a member of the group consisting of H and F, and m is an integer from 1 to 12,

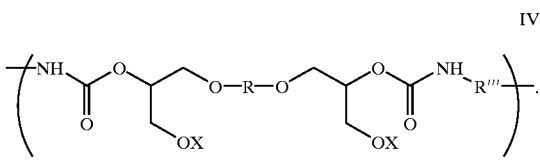

Formulas II and IV represent prepolymers and Formulas IIIa–IIId represent monomers. Both the prepolymers and monomers are useful to be polymerized to make polymers upon curing.

In the prepolymers of Formulas II and IV, n ranges from 2 to sufficient to provide prepolymers having a number average molecular weight of about 19,000. Typical molecular weight is about 12,000. Molecular weight range is about 5000–30,000. Also in Formulas II and IV, the end groups (not shown) are typically acrylate, methacrylate, isocyanato (meth)acrylics, fumarates or maleates.

In Formulas II, IIIa, IIIb, IIIc, IIId, and/or IV. The moieties are defined as follows.

X is selected from the group consisting of moieties V and VI:

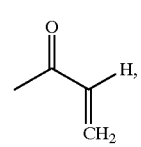

-continued

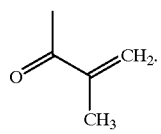
VI

R and R' are selected from the group consisting of moieties VII, VIII, IX, and X:

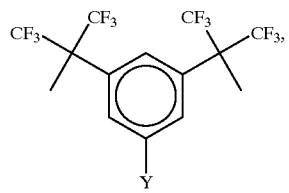
VII

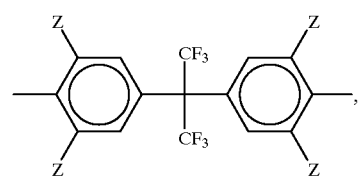
VIII wherein Z is H or Br,

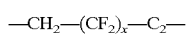
IX, wherein x is an integer from 1 to 12, and

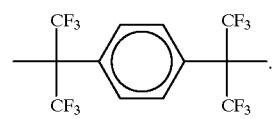
X

Group Y is selected from the group consisting of —H and —(CF$_2$)$_x$F, wherein x is an integer from 1 to 12.

R" is selected from the group consisting of moieties XV, XVI, and XVII:

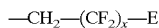
XV, wherein x is an integer from 1 to 16 and E is H or F,

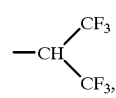
XVI

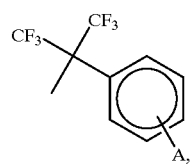
XXVII wherein A is H or —CH$_3$,

R'" is selected from the group consisting of moieties XVIII, XIX, XX, XXa, XXI, XXII, XXIIa, and XXIIb:

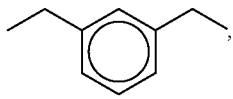
XVIII

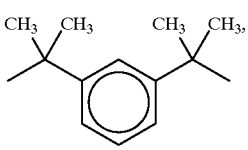
XIX

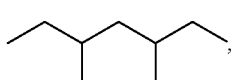
XX

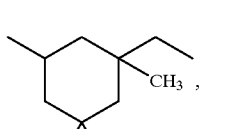
XXa

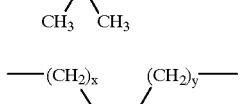
XXI wherein x, y and z are each an integer from 1 to 12,

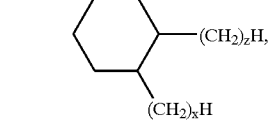
XXII

XXIIa wherein x is an integer from 1 to 12,

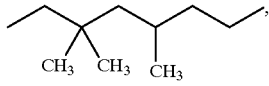
XXIIb

R"" is selected from the group consisting of:

IIIe wherein m is an integer from 1 to 18,

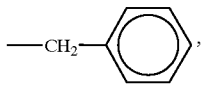
IIIf

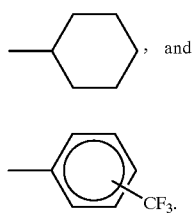

IIIg

, and

IIIh

CF₃.

The polymerizable fluorinated acrylate and methacrylate moieties, both monomers and prepolymers of the present invention contain moderate to high fluorine contents (15 to 65% by mass). The prepolymers may have molecular weights from about 5,000 up to about 30,000, preferably at most about 12,000. Unless stated otherwise, molecular weights in the present specification are weight average molecular weights. The monomers and prepolymers are designed to yield high strength, crosslinked polymers with low surface energies, low water sorption and low polymerization shrinkage. The high strength properties available from the polymers of these monomers and/or prepolymers are related to structural details incorporated in the monomers and prepolymers which include: designs to increase the crosslink density in polymers, rigid backbones to enhance stiffness, and hydrogen bonding via urethane (or other) linkages to reinforce the polymeric network. These structural aspects can be employed separately or combined for greater effect. The potential exists to use liquid crystalline side-chains to further enhance the strength of these materials. Such side chains include linear fluoroalkyl chains, i.e., —$CH_2(CF_2)_x$—F(x=8–16) or —$(CF_2)_x$F. This applies to Y in Formula VII or R" as in Formula XV.

The fluorinated polymers are optically clear and have good solvent resistance, thermal stability, low dielectric constants and low refractive indices. Uses of these polymers include: dental resins and composites, adhesives, protective coatings, optical devices and coatings, and electronic devices. These monomers and prepolymers may be formed into shapes and UV cured to provide an inert dental composite that has low shrinkage and significantly improved durability compared with existing materials.

In its process respects, the present invention also includes a process for preparing fluorinated (meth)acrylate monomers and/or prepolymers which are employable to make fluorinated dental composites based on high strength polymeric networks. The present invention includes a variety of processes to make these monomers and/or pre-polymers.

In the formulas disclosed with this description of the synthesis processes of the present invention, the groups R, R', R", R'", R"", X, Y and n, as applicable, have the same meanings as in the above-described Formulas II, IIIa, IIIb, IIIc, IIId, and IV, unless otherwise indicated.

In a first embodiment of the synthesis process for producing the pre-polymers of Formula II, a diglycidal ether of Formula XXIII is reacted with a hydroxy-containing compound of Formula XXIV at reaction conditions comprising a temperature within the range of about 90° C. to about 120° C. for a time from about 6 hours to about 30 hours, in the presence of about 0.2 to about 2% aromatic or aliphatic tertiary amine or tertiary phosphine catalyst to produce a reaction mixture comprising a moiety of Formula XXIVa. In this process, equivalent mole ratios of XXIII and XXIV are employed to avoid formation of small monomers that would weaken the polymers. Then the reaction mixture is combined with chloro(acrylate) or chloro(meth)acrylate or isocyanato meth(acrylics) at room temperature in the presence of a tertiary amine, e.g., triethylamine, under a nitrogen atmosphere. This process results in the prepolymers of Formula II, as follows:

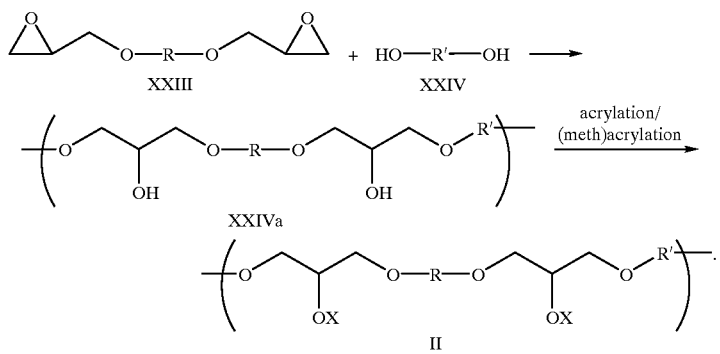

In a second embodiment of the synthesis process for producing the monomers of Formula IIIa, a diglycidal ether of Formula XXV is reacted with a hydroxy-containing compound of Formula XXVI at reaction conditions comprising a temperature within the range of about 90° C. to about 120° C. for a time from about 6 hours to about 30 hours in the presence of tertiary amine or tertiary phosphine, e.g., dimethyl benzylamine or triphenyl phosphine catalyst, followed by acrylation or (meth)acrylation as described above. In this process, excess XXVI (30–50% excess) is employed to increase reaction rate and yield. Unreacted starting material is removed from product by vacuum distillation. This process results in the prepolymers of Formula IIIa, as follows.

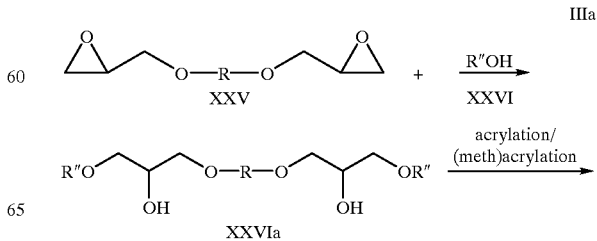

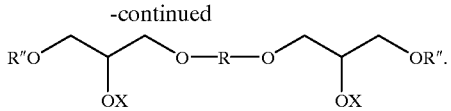

A third embodiment of the synthesis process of the present invention is the following related reaction pathway to fluorinated monomers of Formula IIIb with urethane functionality.

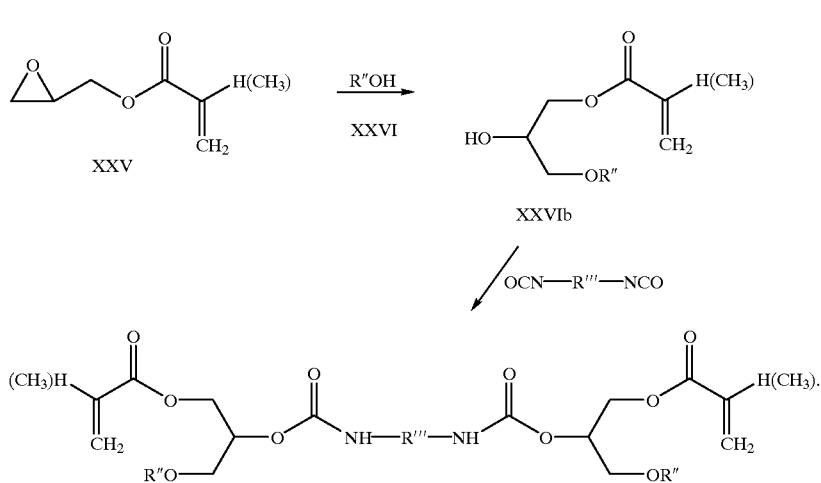

In the third embodiment XXVa and XXVI are reacted at reaction conditions comprising a temperature within the range of about 90° C. to about 120° C. for a time from 6 hours to about 30 hours to produce the reaction product of Formula XXVb. Then XXVb and the diisocyanate of formula OCN—R'''—NCO are reacted at a temperature of from about 20° C. to about 60° C. and for a time of about 2 to about 30 hours to synthesize the prepolymer of Formula IIIb, wherein the groups R" and R''' have the same meaning as in Formula IIIb.

A fourth embodiment of a process for synthesizing the moieties of Formula IIIc comprises the steps of reacting a hydroxy containing compound of Formula XXVIIa:

 XXVIIa, with a glycidyl ether compound of Formula XXVIIIa:

XXVIIIa

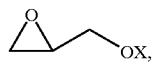

at reaction conditions comprising a temperature within the range of about 60° C. to about 120° for a time from about 6 hours to about 30 hours to produce a compound of Formula XXIX,

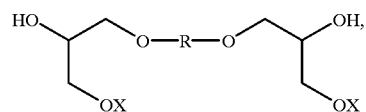

reacting the compound of Formula XXIX with an isocyanate of Formula XXXa:

2 eq OCN—R""      XXXa, at a temperature of about 20° C. to about 60° C. and for a time of about 2 to 30 hours to produce the prepolymer of Formula IIIc;

wherein the groups R and R"" and X have the same meanings as in the Formula IIIc.

A fifth embodiment of a process for synthesizing the moieties of Formula IIId, comprises the steps of:

reacting a hydroxy containing compound of Formula XVIV:

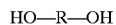 XVIV, with a glycidal ether-containing compound of Formula XXIVa

XXIVa

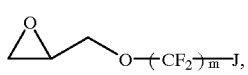

wherein moiety J is H or F and m is an integer from 1 to 12, in the presence of an amine compound comprising a moiety of Formula XXIVb:

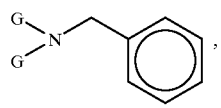

XXIVb

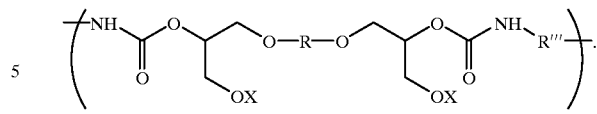

-continued
IV wherein the amine compound is present in an amount of 0.2 to 5.0 mol percent based on weight of compound of Formula XXIVa, preferably each G is independently $CH_3$ or a $C_2$–$C_{12}$ alkyl, at reaction conditions comprising a temperature within the range of about 60° C. to about 120° C., preferably about 80° to about 120° C., for a time from about 6 hours to about 30 hours to produce a compound of Formula XXIXd, The present invention also includes making XXIX by reacting 2 equivalents of glycidyl (meth)acrylate with fluorinated diol (HO—R'—OH).

An alternative process for synthesizing the moieties of Formula IV, comprises reacting a hydroxy containing compound of Formula XXVIIa:

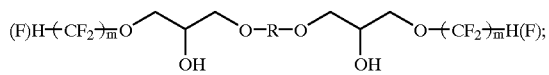

XXIXd

HO—R—OH     XXVIIa, with a glycidyl ether compound of Formula XXVIIIa:

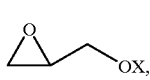

XXVIIIa reacting the compound of Formula XXIXd with a chloromethacrylate or chloroacrylate to synthesize the prepolymer of Formula IIId.

In a sixth embodiment of the synthesis process for producing the pre-polymers of Formula IV, a diglycidyl ether of Formula XXVII is reacted with a vinyl-containing carboxylic acid compound of Formula XXVIII, such as acrylic acid or methacrylic acid, at reaction conditions comprising a temperature within the range of about 60° C. to about 120° C. for a time from about 6 hours to about 30 hours in the presence of tertiary amine, tertiaryphosphine or tertiaryantimony catalyst to produce a compound of Formula XXIX. Thus, acrylate substitution occurs in this first step, unlike the first, second and third embodiments of the processes of the present invention. Then the compound of Formula XXIX is reacted with isocyanate of Formula XXX at a temperature of about 20° C. to about 60° C. and for a time of about 2 to 30 hours. This results in the prepolymers of Formula IV, as follows:

at reaction conditions comprising a temperature within the range of about 60° C. to about 120° C. for a time from about 6 hours to about 30 hours to produce a compound of Formula XXIX,

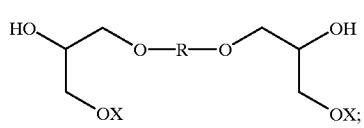

XXIX reacting the compound of Formula XXIX with a diisocyanate of Formula XXX:

OCN—R'''—NCO     XXX, at a temperature of about 20° C. to about 60° C. and for a time of about 2 to 30 hours to produce the prepolymer of Formula IV;

wherein the groups R, R''' and X have the same meanings as in the Formula IV.

A typical example of a first process embodiment may include the following sequential steps A and B for preparing fluorinated prepolymers M-1, M-2, and M-3 from reactants XXXI and XXXII as follows:

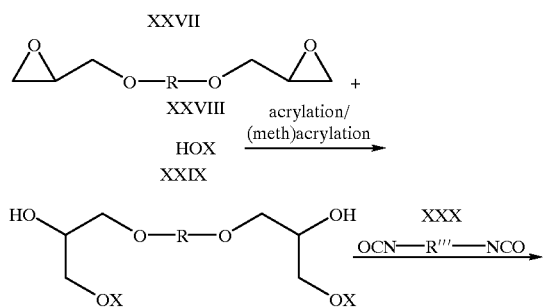

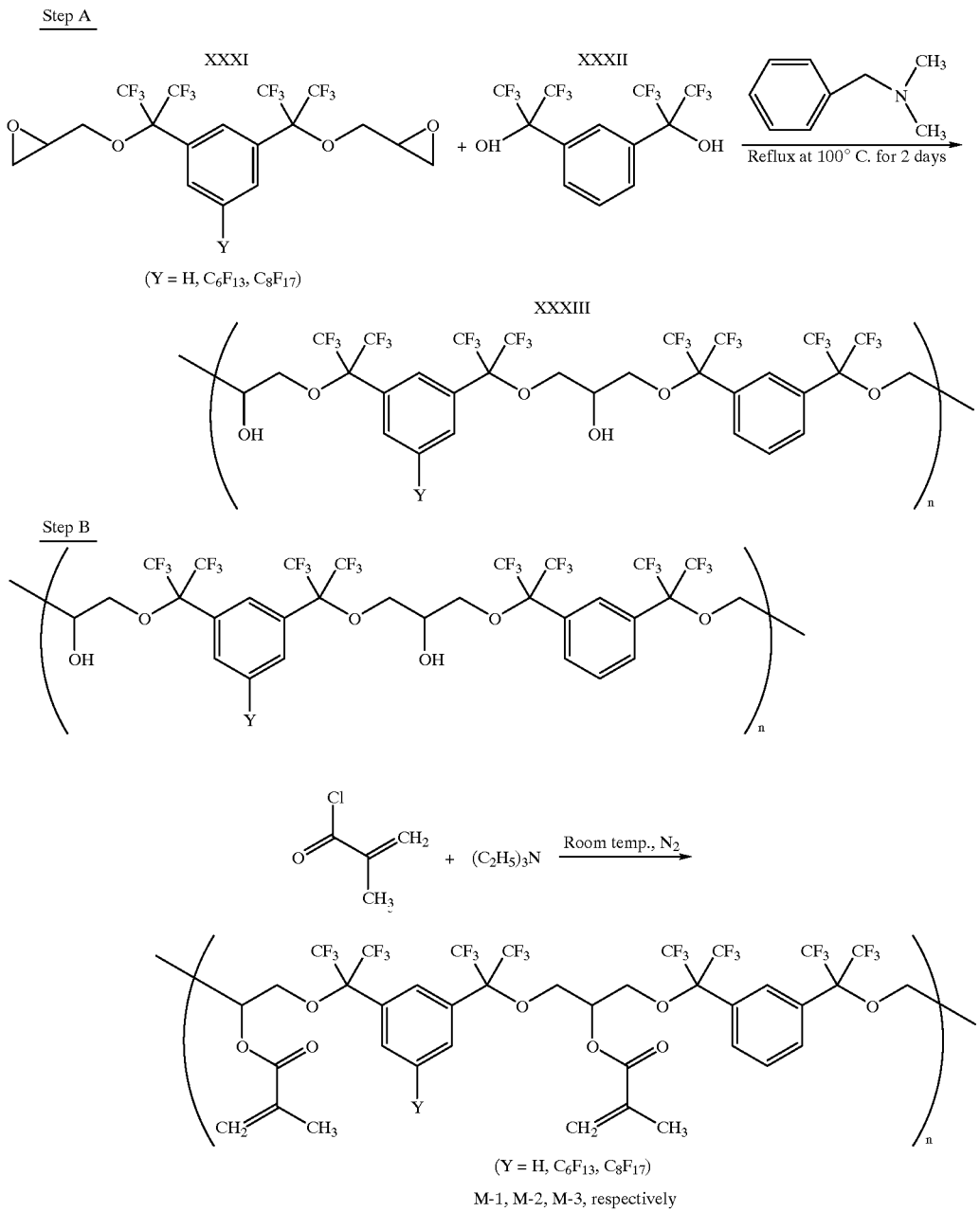

(Y = H, C₆F₁₃, C₈F₁₇)
M-1, M-2, M-3, respectively

In the above moieties XXXIII and XXXVI, n is sufficient to obtain the desired prepolymer XXXVI molecular weight.

The above processes of the present invention produce monomers and/or prepolymers in which the pendant methacrylate functionality is separated by spacer groups that serve to decrease the density of reactive sites and thereby reduce polymerization shrinkage. The oligomeric nature of the fluorinated prepolymers enhances the crosslink density in the fluoropolymers to compensate for otherwise low cohesive energies. This aids in producing fluorinated polymers with good mechanical strength properties. The introduction of fluorinated substituents aids in achieving lower viscosities than would be obtained with similar hydrocarbon oligomers. This technique also minimizes biocompatibility concerns related to leachable components.

The monomers and/or prepolymers may be employed to make compositions of the present invention by adding any of the following ingredients: diluent co-monomer, e.g., triethylene glycol dimethacrylate, to control viscosity, initiator, e.g., for visible light or UV curing, and/or fillers, e.g., ground glass or quartz.

The present invention has many advantages. The introduction of covalently bound organofluorine into dental resins offers a technique to dramatically reduce water uptake, eliminate discoloration and improve the fracture toughness of composites. Through appropriate design of the fluoromonomers and/or fluoroprepolymers, both low polymerization shrinkage and excellent mechanical strength can be attained in these materials.

The design of fluorinated monomers and/or prepolymers capable of rapid efficient polymerization to yield inert, crosslinked polymeric networks offers a means to avoid the processing problems encountered with thermoplastic fluoropolymers.

The present invention provides new families of fluoromonomers and/or fluoroprepolymers designed to improve the performance of aesthetic dental polymeric restorative materials. The present invention includes several types of moderately to highly fluorinated methacrylate-based monomers and/or prepolymers. The monomers and/or prepolymers are useful to prepare new fluoropolymers which exhibit excellent hydrophobicity and physical strength. In principle, these properties are inversely related; the physical strength of polymers rich in fluorine is generally reduced by increasing fluorine content due to the low cohesive energy associated with fluoropolymers.

The present invention is illustrated by the following non-limiting examples. In the Examples a number of parameters were measured by the following methods:

1. Refractive Index Measurements

Refractive indices of the fluoromonomers and the resins with 1,10-decamethylene glycol dimethacrylate (DMDM) were measured using a refractometer (Bausch & Lomb Optical Co. 33-45-58) at 23.5° C.

2. Water Contact Angle Measurements

Photocured composite disks measuring 15 mm×0.75 mm were prepared for water contact angle measurements. A goniometer (Rame-Hart Inc., Mountain Lakes, N.J.; NRLC) was used to measure the static contact angle of deionized water on these composite disks. The surface of the disks was cleaned with both water and hexane before the measurements. Small drops of deionized water (<2 mm diameter) were placed on the surface of the disks using a syringe. The contact angles were measured within 30 sec of water application. Three measurements were made on both sides of the disks and the results were averaged.

3. Transverse Strength (TS) Measurements (also known as Flexural Strength (FS) Measurements)

Filled composites were photocured in a mold to provide bar-shaped specimens (27 mm×3.5 mm×0.75 mm). The TS of photocured composite specimens was determined using a 3-point bending test fixture with a span of 10 mm on a universal testing machine (Instron Corp., Canton, Mass.: 5500 R) operated at a crosshead speed of 1 mm/min. The transverse strength was calculated using an integral software program (Instron Corp., MERLIN software).

4. Water Uptake Measurements

The relative hydrophobicity of the fluorinated composites was evaluated by measurement of the equilibrium water uptake. The mass of dried disks (15 mm×0.75 mm) used for contact angle determination were initially measured. The samples were then immersed in distilled water for 2 weeks. All samples attained a constant weight by this time. The water uptake, as a percentage of the preimmersion sample mass, was calculated from the difference between the mass of the initial dried disks and the final water-equilibrated mass.

5. Density Measurements

The dried disks used for contact angle and water uptake measurements were also utilized in determination of the density of the fluorinated composites. Densities were measured using a micropycnometer (Quanta Chrome Corp.: MPY-2) with helium gas. 6. Polymerization Shrinkage Measurements Photopolymerization shrinkage of unfilled resins or resins containing 5–20 mass % of a microfine glass filler (OX-50, Degussa, added to increase resin viscosity) was measured using a computer-controlled mercury dilatometer. The reported polymerization shrinkage values for those resin samples requiring the addition of the thickening agent have been corrected to account for the amount of resin displaced by the filler. The activated resin specimen (approximately 30 mg) was placed on a glass slide (quartz plate). A glass ball joint was clamped over the specimen and filled with mercury so that the specimen was completely covered. A linear variable displacement transducer (LVDT) was set on the surface of the column of mercury. A visible light dental curing device (MAX LIGHT, Dentsply International Inc.) was placed beneath the sample slide for photocuring. A microcomputer simultaneously records both the height of the mercury, from the LVDT output, and the temperature of the mercury, from a thermistor in contact with the mercury. The activated resins were photocured by irradiation with visible light (470 nm) for 60 seconds. The software triggers the cure light and collects data from the LVDT and thermistor. At the end of 2 hours, the run was terminated and the software calculated the percent shrinkage based on mercury height change (with the temperature effect factored out), the specimen weight, and the specimen density. The densities of photocured resins were measured by applying the Archimedean principle of specific gravity determination based on weight difference in air and liquid. An analytical balance (Sartorius Corp. YDK 01) with a density measurement accessary was used.

7. Gel-Permeation Chromatography (GPC) Measurements Samples of each oligomeric fluoromonomer were dissolved in tetrahydrofuran and analyzed by GPC (Waters Associates Inc.: 150-C, ALC/GPC). A 500 mm×10 mm column (Jordi Mixed Bed # 11) was used at a flow rate of 1 mL/min. A commercial multimodal polystyrene mixture (EASY CALC) was used as a calibration standard

EXAMPLES

Comparative Example

This comparative example involves a control resin of Bis-GMA and TEGDMA dimethacrylate monomers because dental resins and composites based on the combination of Bis-GMA and TEGDMA dimethacrylate monomers are widely used. Typical properties of unfilled photocured resins comprised of Bis-GMA/TEGDMA (7:3 mass ratio) include a polymerization shrinkage of 7.9% by volume, a diametral tensile strength (DTS) and flexural strength (FS) of 42.2 MPa±3.6 MPa and 75.3 MPa±4.3 MPa, respectively. A particulate glass-filled composite based on the Bis-GMA/TEGDMA resin(mass fraction of 80% filler) produced DTS and FS values of 50.5 MPa±1.3 MPa and 91.4 MPa±8.5 MPa, respectively. The equilibrium water uptake of a Bis-GMANTEGDMA resin (7:3 mass ratio) is 3.8% (mass fraction) for the unfilled resin and 1.2% (mass fraction) for a composite containing silanized quartz filler (filler-resin mass ratio of 2:1). Since there are other conventional hydrocarbon dimethacrylate monomers that are more hydrophobic than Bis-GMA and TEGDMA, a second control resin composed of ethoxylated bisphenol A dimethacrylate (EBPAD; Esschem) and 1,10-decanediol dimethacrylate (DMDM) was also examined for comparison with the fluorinated resins developed here.

A. Syntheses of Monomers of the Present Invention

As shown in Scheme 1, a number of interrelated synthetic routes (paths A–D) to fluorinated monomers and oligomers were examined. All of these techniques rely on the facile epoxide ring-opening addition reaction with either methacrylic acid or relatively acidic fluorinated alcohols. While similar in this general theme, the multifunctional oligomeric monomers produced differ substantially in overall structure, organofluorine content and the types of polymerizable groups they contain. The synthetic approaches used in the present invention leave the methacrylate ester groups far removed from the strong electron withdrawing effects of the fluorinated substituents. The insulation of the ester groups from the fluorinated substituents should promote acceptable levels of hydrolytic stability in these methacrylate esters that can not be achieved by direct esterification of the majority of available fluorinated alcohol or diol starting materials. The avoidance of potential hydrolytic stability problems for the polymer matrix is a serious consideration for materials designed for long-term durability in the oral environment. Scheme 1 is shown as Parts 1, 2 and 3. The parts are all connected.

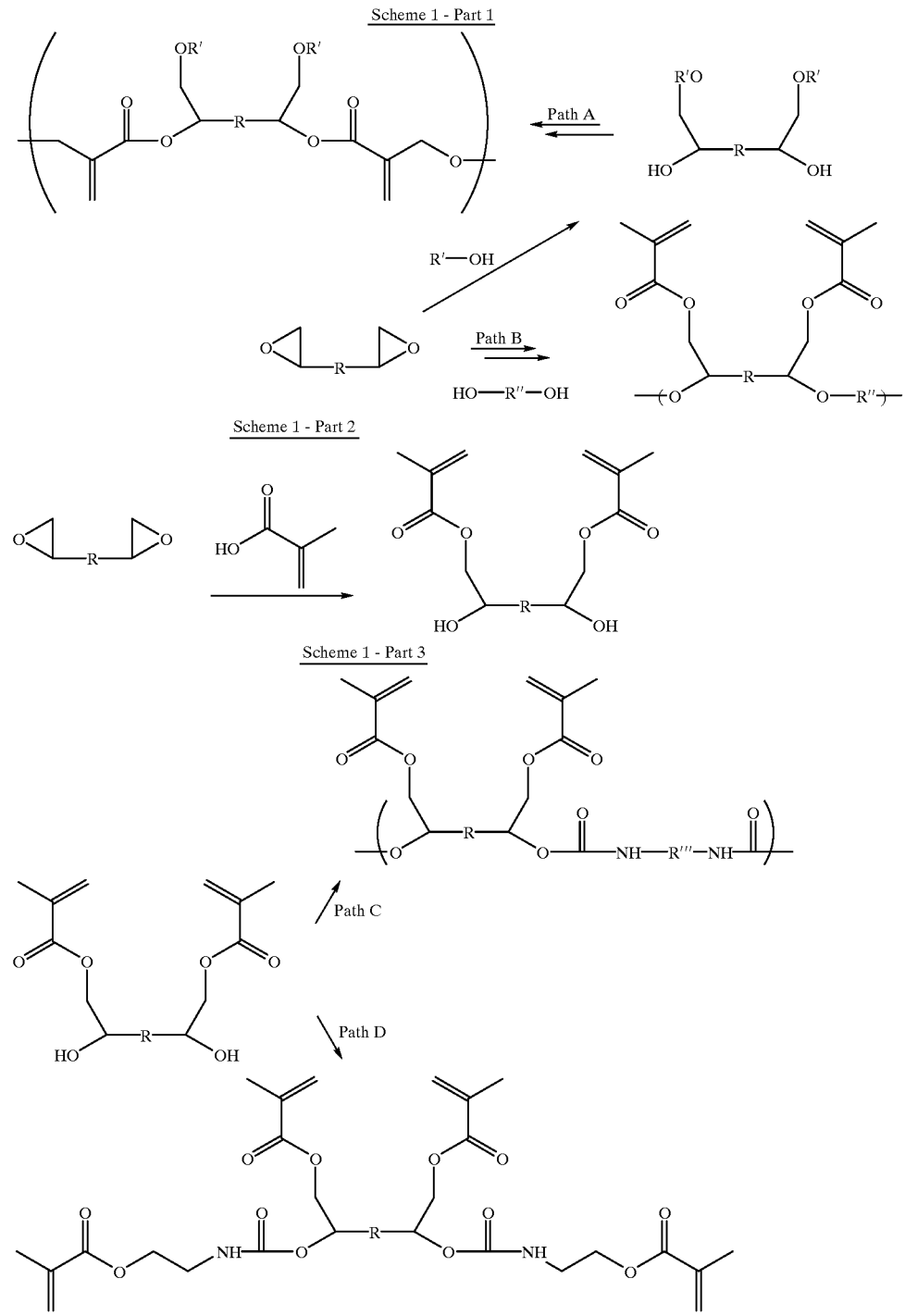

For the most part, diepoxides were used as starting materials for the synthesis of the fluorinated methacrylates. The reactive multifunctional oligomeric approach was adopted in most cases because it offers increased cross-link densities compared with simpler dimethacrylated monomers at comparable levels of conversion. The use of multifunctional ooigomers also minimizes the presence of pendant chains that remain in the polymerized network structures. Typically, the ambient temperature photopolymerization of dimethacrylate dental resins produces vitrified polymers with cross-link efficiencies of only about 20%. Therefore, the majority of the difunctional monomer units are incorporated into polymer as half-reacted pendant methacrylate terminated chains. This aspect may be especially important in the development of fluorinated polymers with good mechanical strength properties. Due to the low cohesive energy associated with fluorinated polymers, excessive amounts of pendant chains may be very detrimental to the glass transition temperature, modulus and strength properties attainable with these resin systems. A recent evaluation of a series of fluorinated dimethacrylate monomers, which varied in fluorine mass fraction from 23% to 61%, demonstrated that strength properties of the resulting photocured polymers generally decreased with increasing fluorine content and that all the strength values obtained for the fluorinated materials, even those with relatively modest fluorine contents, were significantly less that those of the Bis-GMA/TEGDMA hydrocarbon control material. The oligomeric fluorinated monomers are expected to reduce or eliminate this disparity in strength and thereby allow the incorporation of higher levels of fluorine without the sacrifice of mechanical strength. Finally, the use of relatively high molecular weight oligomers in the resins tends to minimize potential toxicity concerns for materials under consideration for intra-oral application.

The progress of the epoxy ring-opening reactions were monitored by $^1$H NMR spectroscopy on aliquots removed from the neat reaction mixtures. The disappearance of the three distinctive epoxy proton signals in the spectra between 2.5 ppm and 3.5 ppm was readily apparent. Scheme 2 shows the major and minor isomers (A and B, respectively) produced by the epoxide ring opening. The integrated NMR spectra indicate that the less hindered approach of the fluoroalcohol to generate the secondary alcohol product (A) was favored over the more hindered attach to yield the primary alcohol by approximately 4:1. For simplicity, the subsequent figures display only the more prevalent isomers.

Scheme 2

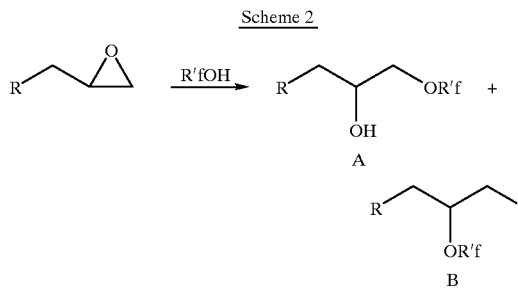

The synthesis of oligomers by path A (Scheme 1) was devised to take advantage of the high degrees of conversion and the low polymerization shrinkage available through a novel cyclopolymerization process. The polymerization of difunctional monomers by an efficient cyclization process can reduce shrinkage by approximately 30% compared with conventional dimethacrylated monomers. The 1,4- diazabicyclo(2,2,2)octane (DABCO)-catalyzed addition of formaldehyde to acrylated followed by condensation between the resulting α-hydroxymethylate intermediates provides monomers with 1,6-diene structures capable of efficient cyclopolymerization (Scheme 3a).

Scheme 3a

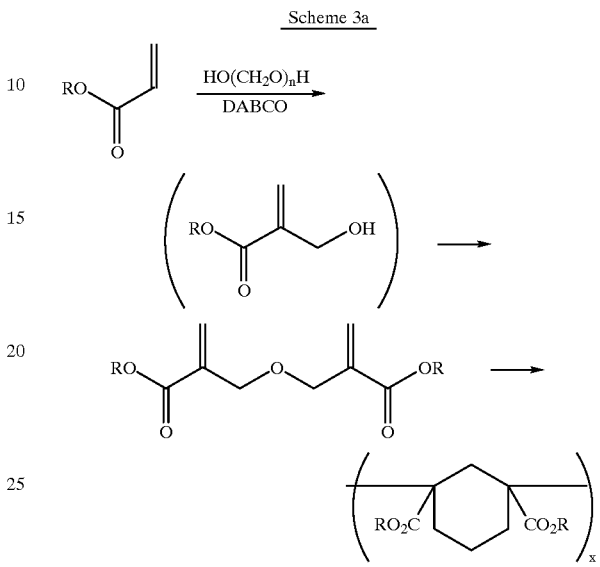

Previously, difficulties were encountered in the synthesis of cyclopolymerizable monomers from fluorinated acrylate starting materials. The predominant product formed with these electron deficient acrylate esters was a 1,4-diene (Scheme 3b) rather than the expected cyclopolymerizable 1,6-diene product.

Scheme 3b

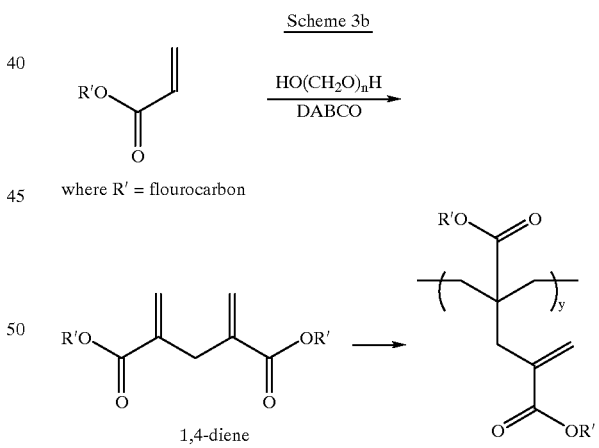

where R' = flourocarbon 1,4-diene

The insulation of the fluorinated substituents from the acrylate functionality in the present invention leads to smooth conversion to the desired 1,6-diene linkages. The chain extension of diacrylates via the formation of cyclopolymerizable 1,6-diene units has been studied and applied to hydrocarbon-based dental resin applications. In this case, the 1,6-diene group is an integral component of the ohigomer backbone (Scheme 3c) and the free radical cyclopolymerization results in cross-link formation with low polymerization shrinkage.

Scheme 3c

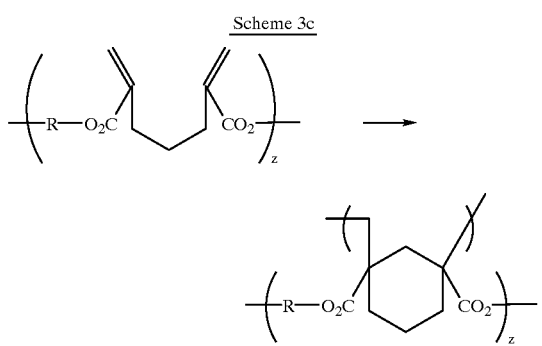

The synthesis of cyclopolymerizable fluorinated oligomers 3a and 3b of the Examples is detailed in Scheme 4. The multifunctional oligomers are derived from the diglycidyl ether of bisphenol A and its tetrabrominated analog, respectively. The diepoxide ring-opening addition with heptafluorobutanol in the presence of N,N-dimethylbenzylamine produced fluorinated diol intermediates that were subsequently converted to the diacrylates. The final step involves the transformation of the acrylate groups to α-hydroxymethylacrylates, which then condense to form the linear oligomeric products containing the cyclopolymerizable 1,6-diene linking groups in the backbone. In 3b, the bromine substitute is included primarily to increase the refractive index of the resulting oligomer.

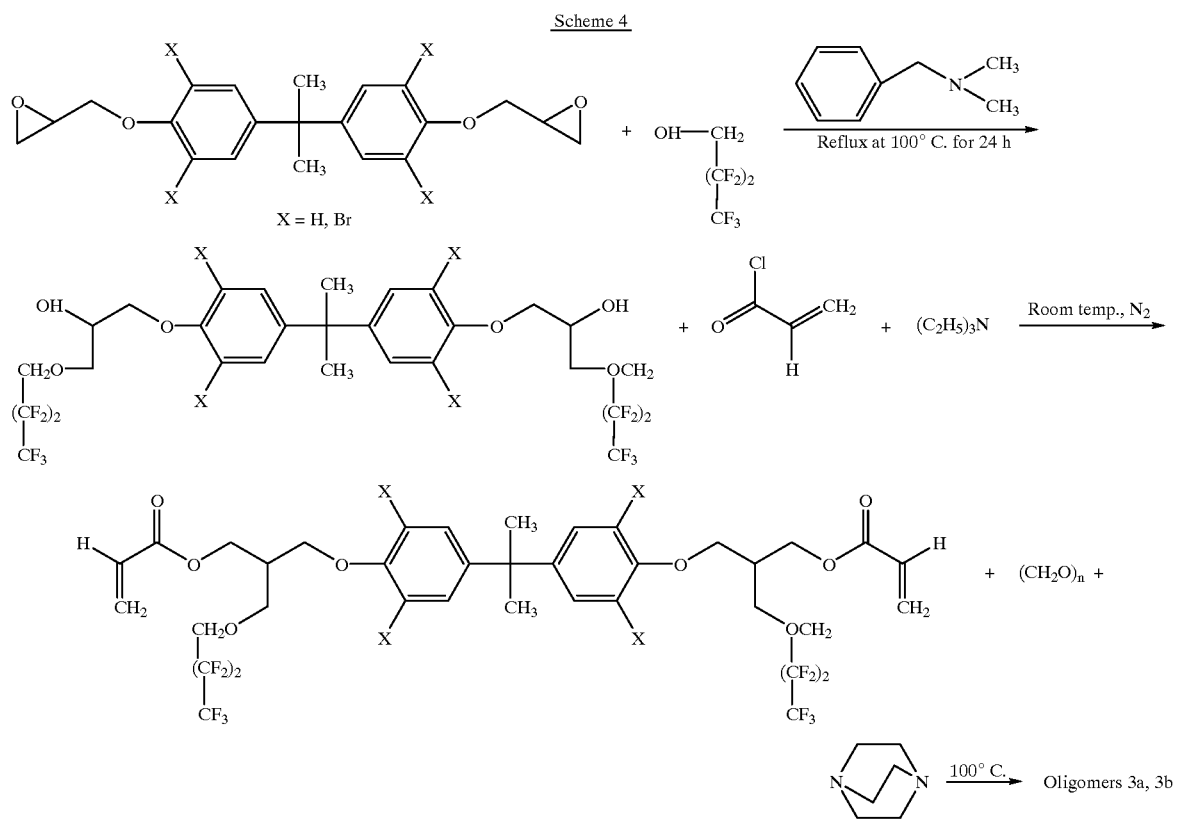

Scheme 4

A variation of this cyclopolymerizable oligomer synthetic approach was used to prepare a highly branched multifunctional oligomer 6 (Scheme 5). The tefrafunctional nature of the starting epoxide and acrylate intermediate required that the final oligomerization step be stopped at relatively low conversion to avoid gelation.

Scheme 5

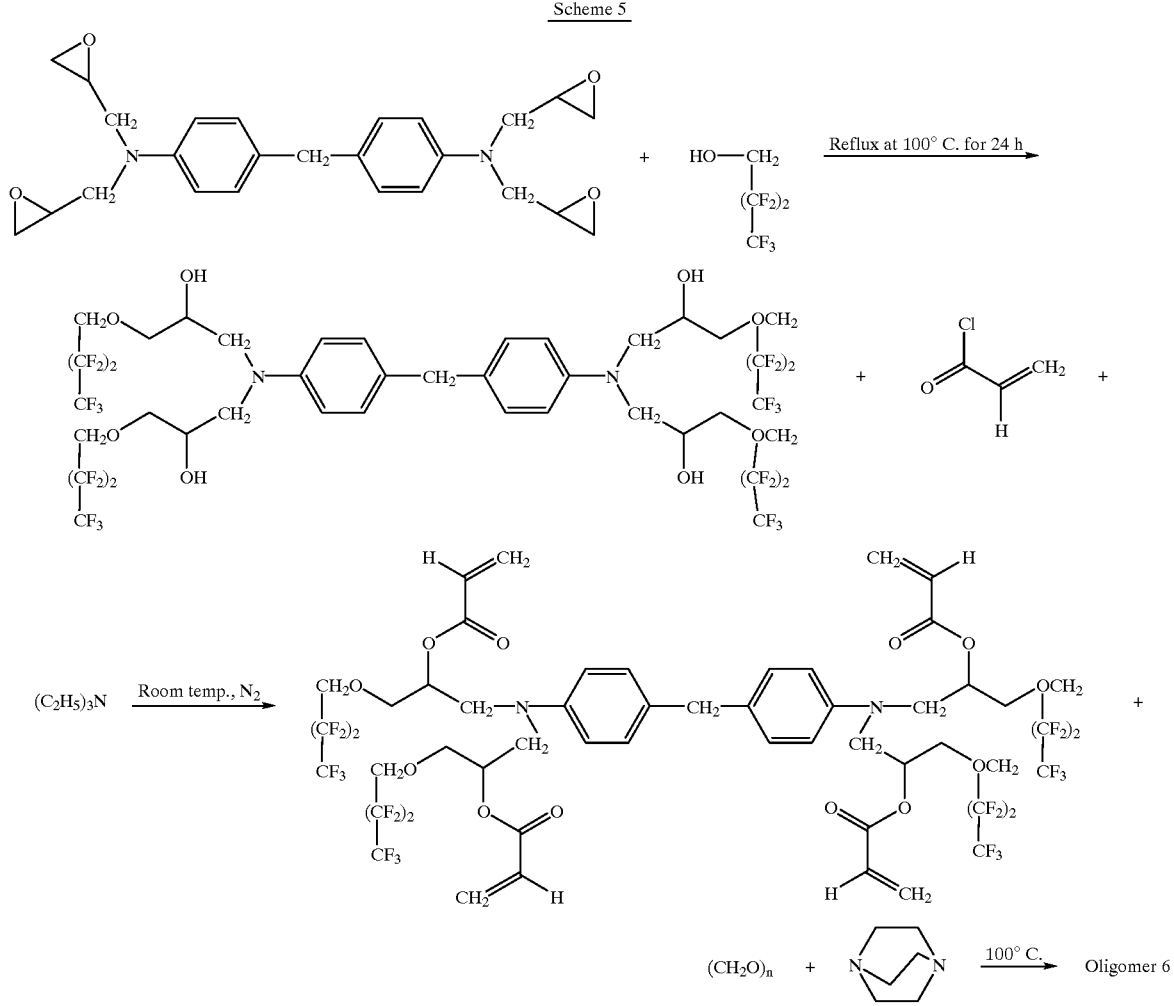

The preparation of fluorinated oligomers 8a–c (Scheme 6) relies on the direct oligomerization (path B, Scheme 1) using a fluorinated aromatic diol and a structurally similar fluorinated diepoxide that can include an additional perfluoroalkyl chain. Polymerizable methacrylate groups were then appended to the resulting polyol intermediates (Scheme 6) to produce the final oligomers. The addition of the perfluorosidechains offers the ability to vary the overall fluorine content and modify physical properties of the oligomer, such as viscosity. The mass percentages of fluorine in oligomers 8a, 8b and 8c are relatively high at 42.7%, 50.7% and 52.4%, respectively.

Scheme 6

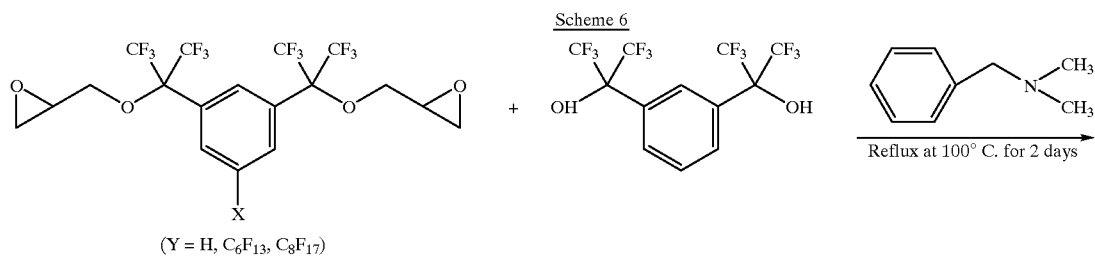

(Y = H, $C_6F_{13}$, $C_8F_{17}$)

-continued

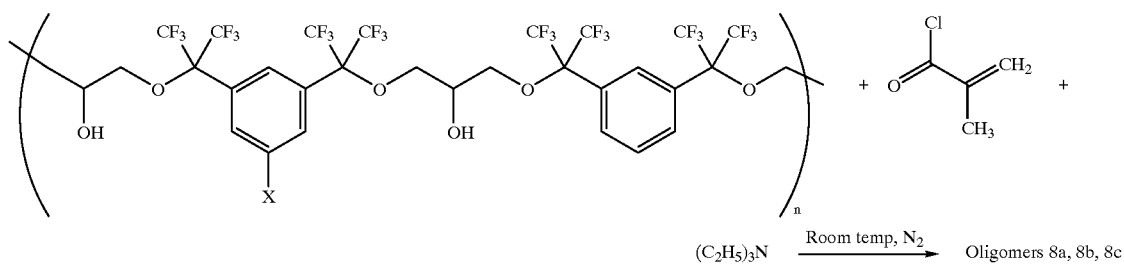

A related ring-opening additional reaction between a fluorinated diepoxide and two equivalents of methacrylic acid was used to prepare a series of fluorinated diol dimethacrylate intermediates 9 (Scheme 7—Part 1). Some of the same diol intermediates were also prepared by the parallel reaction that relied on the combination of a fluorinated diol with two equivalents of glycidyl methacrylate. Both synthetic routes of Scheme 7—Part 1 provide high yields of the diol dimethacrylate intermediates 9. However, the latter route is important to establish the general utility of this reaction since there are many fluorinated diols commercially available. As shown generally in path C of Scheme 1 and specifically in Scheme 7, the diol intermediates 9 obtained from the epoxide ring-opening reactions were chain-extended with an aliphatic duisocyanate (DDI 1410, Henkel Corp.) derived from dimer acid. This diisocyanate was selected since it offers a bulky, hydrophobic spacer group that can contribute to reduced polymerization shrinkage. The resulting urethane-linked methacrylate oligomers 10a and 10b were isolated as extremely viscous liquids.

Scheme 7-Part 1

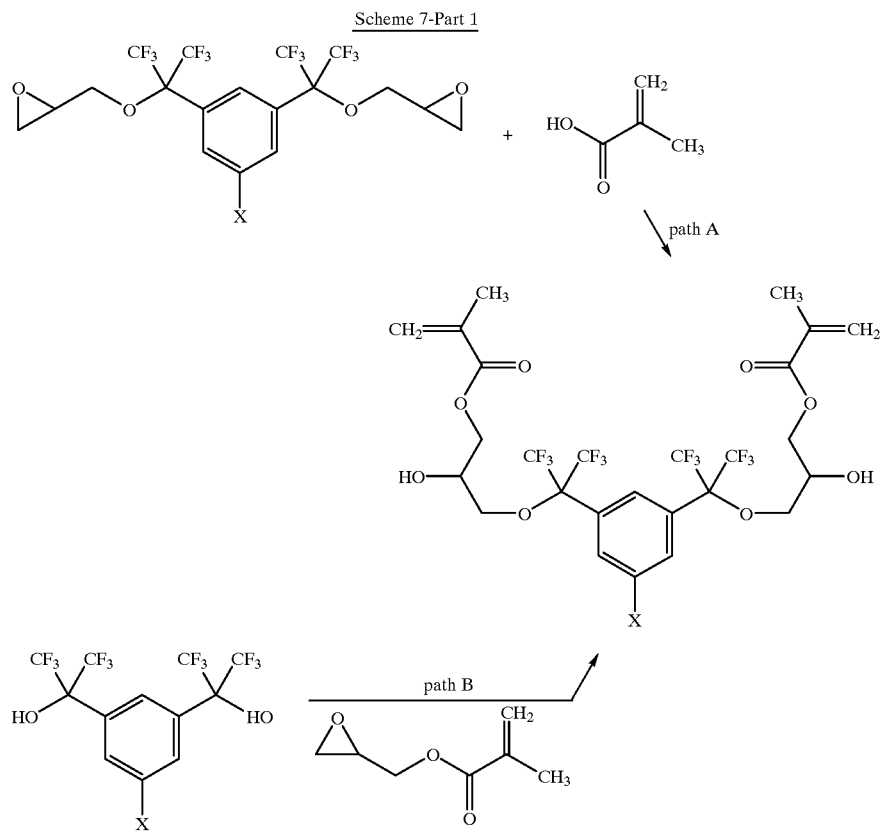

-continued
Scheme 7-Part 2

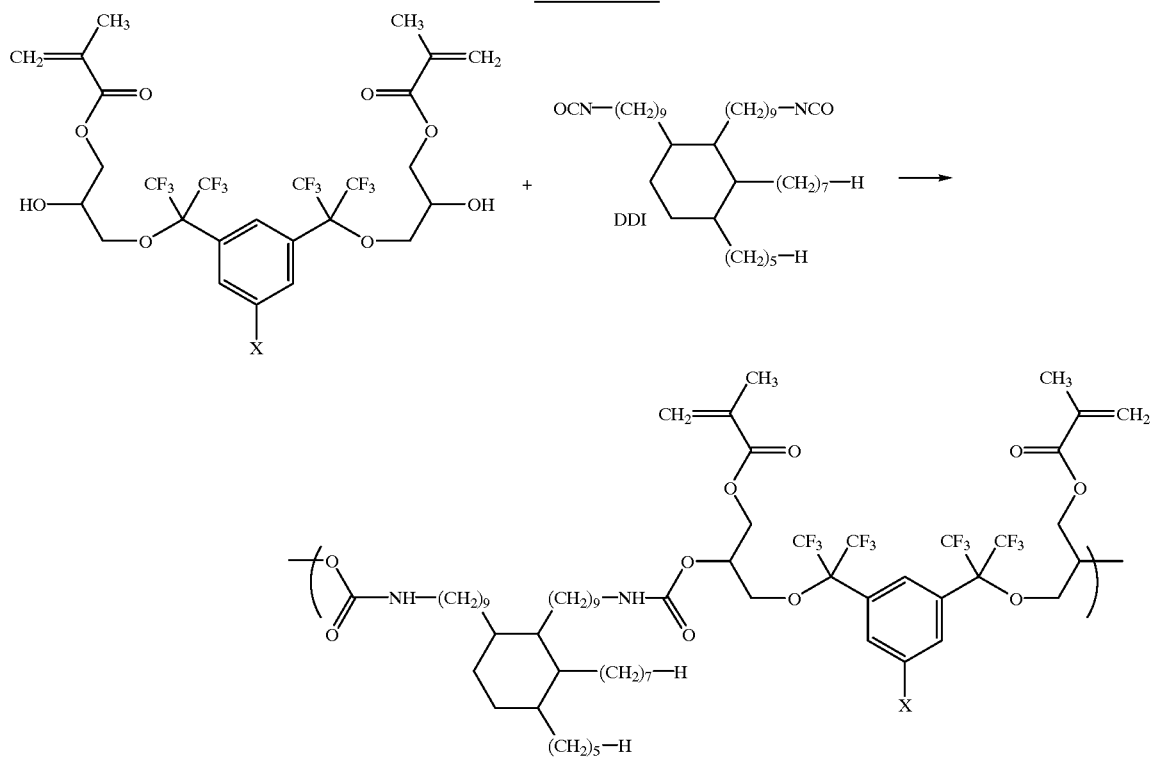

10a: X = H
10b: X—C$_8$F$_{17}$
Monomers 10a, 10b of Examples

In a separate synthetic technique, a difunctional fluorinated monomer, rather than a multifunctional oligomer, was also prepared for evaluation. This approach also utilizes the addition of a fluorinated alcohol to an epoxide ring, glycidyl methacrylated in this case. The resulting hydroxy-substituted fluorinated methacrylate was then combined with an aromatic diisocyanate to give a dimethacrylate with urethane functional groups (Monomer 12 of the Examples, Scheme 8). In another synthesis to prepare a discrete monomer rather than oligomer, a tetrafunctional urethane-containing monomer (Monomer 13 of the Examples) was obtained by fluorinating the diol dimethacrylate intermediate of Scheme 7 and the addition of isocyanatoethyl methacrylate to the fluorinated diol dimethacrylate.

Scheme 8

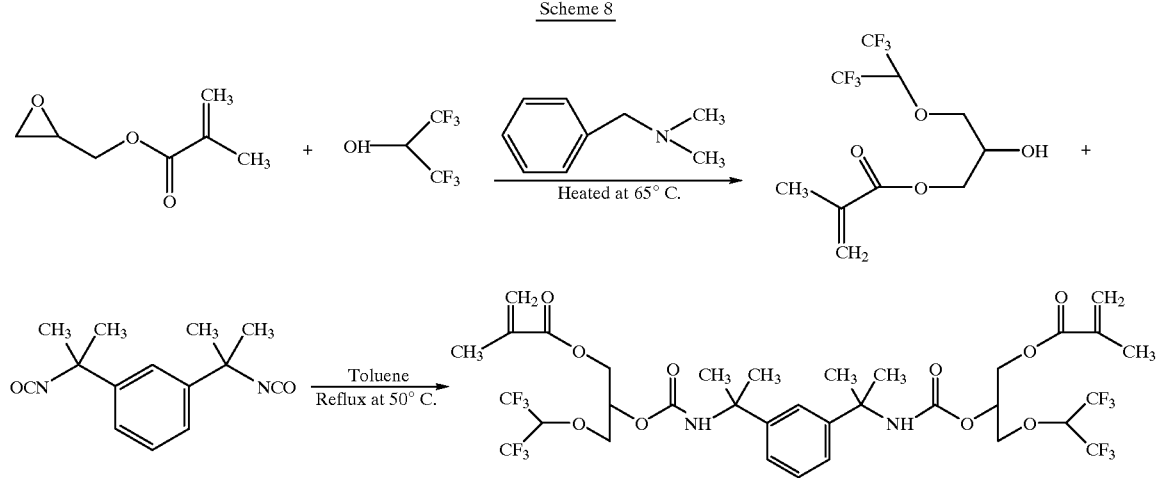

A. Monomer synthesis

All the products and intermediates were characterized with Fourier transform infrared (FT-IR, NICOLET MAGNA 550) and nuclear magnetic resonance ($^1$H and $^{13}$C NMR, JEOL GSX-270 MHZ, tetramethylsilane as internal standard) spectroscopies.

Example 1

Synthesis of 3a

Diglycidyl ether of bisphenol A (DER 332: Dow Chem. Co.) 10.00 g, 29.4 mmol) and 23.52 g (0.1 mol) of heptafluoro-1-butanol were combined in a flask. After 0.20 g (1.46 mmol) of N,N-dimethylbenzylamine was added, the flask was heated at 100° C. for 24 h. The reaction was monitored by the disappearance of the epoxy peaks in the $^1$H NMR spectra. Removal of the excess fluoroalcohol under reduced pressure provided, 18.50 g (0.025 mol) of the diol intermediate as a yellow viscous liquid, which was dissolved into 6.30 g (0.0625 mol) of triethylamine in chloroform (50 mL). The solution was cooled in an ice bath (0° C.) for 20 minutes with stirring and $N_2$ purging. Acryloyl chloride (4.75 g, 0.05 mol) in chloroform (20 mL) was then added dropwise. After the addition of acryloyl chloride was complete, the ice bath was removed, and the reaction mixture was stirred under $N_2$ at room temperature for 24 h. The crude reaction mixture extracted with HCl (0.1 mol/L) to remove the amine salts. The solvent was removed under a reduced pressure to leave a dark brown liquid residue. The difunctional methacrylate (22.61 g, 0.027 mol) was transferred to a heavy-walled bottle with a screw-cap. Paraformaldehyde (1.60 g, 0.054 mol) and 0.60 g (5.4 mmol) of 1,4-diaza-bicyclo(2,2,2)octane (DABCO) were also added. After the addition of a trace of DMSO as solvent, the mixture was sealed and heated in an oven at 100° C. for 2 days. A yellow-brown viscous oligomeric product was obtained. The product was precipitated from hexane and washed with several portions of hexane to remove the low molecular weight components. The oligomer was dissolved in dichloromethane and purified by filtration through silica gel. The solvent was removed under reduced pressure to leave the oligomer product as a viscous pale-yellow liquid. Polystyrene equivalent molecular weights of this oligomer by gel-permeation chromatography (GPC) were 1004, 1906 and 5839.

Monomers 3a, 3b have the Formula 3a, 3b, where in Formula 3a, X is H or in Formula 36, X is Br:

Example 2

Synthesis of Monomer 3b

A procedure similar to that described for the synthesis of 3a was used to convert the diglycidyl ether of 3,3',5,5'-tetrabromo bisphenol A (DER 542: Dow Chem. Co.) to the brominated oligomer. The oligomeric product was obtained as a light brown viscous liquid. GPC analysis of the oligomeric product provided polystyrene equivalent molecular weight peaks at 1047, 1950 and 6669.

Example 3

Synthesis of Monomer 6

4,4'-Methylene bis(N,N-diglycidylaniline) (15.00 g, 0.035 mol) and 1H, 1H-heptafluoro-1-butanol (35.50 g, 0.47 mol) was heated at 100° C. for 24 h. The epoxy resin of the NMR spectrum was monitored to determine completion of the reaction. The light brown liquid product was purified by column chromatography with hexane/diethyl ether (1/9, v/v) as eluant. After removal of the solvent, a yellow liquid was obtained. The product (30.32 g, 0.025 mol) was transferred in a three-neck flask with additional funnel. Triethylamine (11.14 g, 0.11 mol) in chloroform (10 mL) was added in the flask. The solution was cooled in an ice bath (0° C.) under $N_2$. Then, acryloyl chloride (9.60 g, 0.1 mol) in chloroform (10 mL) was added dropwise. After the addition was completed, the ice bath was removed and the reaction flask was stored at room temperature for 5 h. The resulting dark-yellow liquid was extracted with aqueous HCl (0.01 mol/L). The organic phase was dried over sodium sulfate anhydrous and the solvent evaporated under reduced pressure to yield 21.35 g (0.015 mol) of a brown liquid residue. The product was transferred to a screw-capped bottle along with paraformaldehyde (1.82 g, 0.06 mol), 1,4-diazabicyclo (2,2,2)octane (DABCO; 0.67 g, 5.97 mmol), and a trace amount of DMSO. The bottle was shaken to mix the reactants completely and then heated in an oven at 100° C. for 5 h. The oligomeric product was washed with hexane to remove any low molecular weight material. The oligomer was dissolved in dichloromethane and filtered to remove any cross-linked product. The solvent was removed under reduced pressure to give 6 as a viscous light brown liquid. Monomer 6 is a compound of Formula 6.

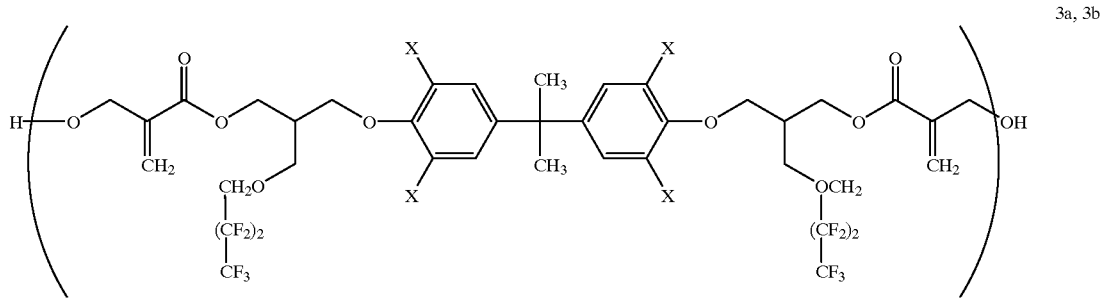

3a, 3b

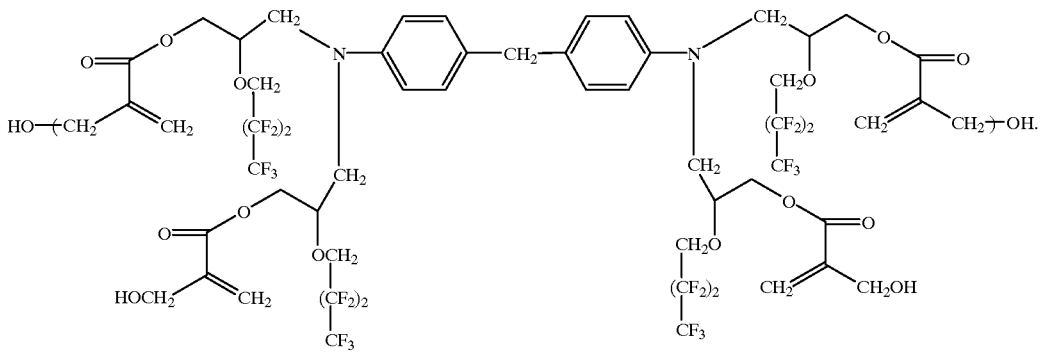

6

Example 4
Synthesis of 8a (also labelled M-1)

1,3-Bis(hexafluoro-2-hydroxypropyl)benzene diglycidyl ether (10.90 g, 0.021 mol) and α,α,α',α'-tetrakis(trifluoromethyl)-1,3-benzene-dimethanol (8–57 g, 0.021 mol) were heated to 100° C. for 2 days with 0.14 g (1.04 mmol) of N,N'-dimethylbenzylamine as catalyst for the epoxy ring-opening reaction. The viscosity of the reaction mixture increased along with the molecular weight of the resulting oligomer as the reaction proceeded. The polymerization was monitored by the disappearance of the epoxy peaks in $^1$H NMR spectra. This resulted in a yellow, viscous polyol intermediate.

The polyol intermediate was converted to the multimethacrylate oligomer by reaction with 2.5 equivalents of triethylamine and 2.1 equivalents of methacryloyl chloride in chloroform for 12 hours at room temperature. In particular, the intermediate product, 15.94 g (0.017 mol) of the yellow viscous polyol, was dissolved in chloroform (40 mL) and combined with triethylamine (4.31 g, 0.04 mol). Methacryloyl chloride (3.75 g, 0.0357 mol) in chloroform (10 mL) was added dropwise to the stirred solution. The reaction mixture changes from yellow to a light red-brown during the addition. The reaction was continued under $N_2$ at room temperature for 12 hours.

The product was extracted with 1 mol/L HCl to remove the amine salts and passed through a silica pad to remove the color. The solvent was evaporated under reduced pressure to leave monomer M-1 as a light brown, sticky, viscous residue. GPC analysis of the oligomeric product provided polystyrene equivalent molecular weight peaks at 1,103 and 17,175.

Example 5
Synthesis of 8b (also labelled M-2)

A procedure similar to that described for the synthesis of M-1 was followed to prepare a multifunctional monomer from 1,3-bis(hexafluoro-2-hydroxy-propyl)-5-perfluorohexyl benzene diglycidyl ether and α,α,α',α'-tetrakis(trifluoromethyl)-1,3-benzene-dimethanol. The product was dissolved in dichloromethane and passed through silica gel to remove the color. Evaporation of the solvent under reduced pressure produced the polymeric product as a light brown viscous residue. GPC analysis of the oligomeric product provided polystyrene equivalent molecular weight peaks at 1,186 and 7,169.

Example 6
Synthesis of M-3 (also labelled 8c)

A procedure similar to that described for the synthesis of M-1 was followed to prepare a multifunctional monomer from 1,3-bis(hexafluoro-2-hydroxypropyl)-5-perfluorooctyl benzene diglycidyl ether and α,α,α',α'-tetrakis(trifluoromethyl)-1,3-benzene-dimethanol. The product was dissolved in dichloromethane and passed through silica gel to remove the color. Following solvent evaporation under reduced pressure the polymeric product remained as a light brown viscous residue. GPC analysis of the oligomeric product provided polystyrene equivalent molecular weight peaks at 1374, 2168, and 4480.

Monomers 8a, 8b, 8c have the Structure of Formula 8a, 8b, 8c, wherein X=H, $C_6F_{13}$, $C_8F_{17}$, respectively:

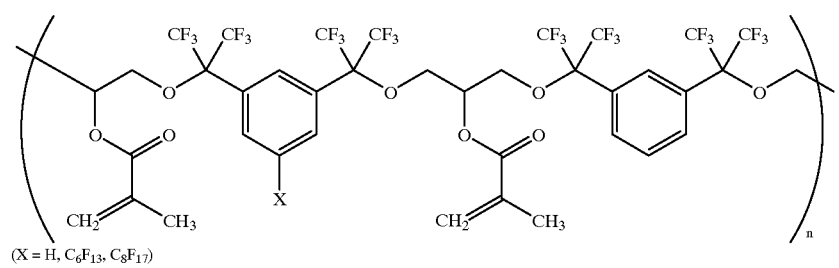

8a, 8b, 8c

Example 7
Synthesis of 10a

Two separate synthetic routes were used to prepare the diol dimethacrylate intermediate necessary for 10a. In the first procedure, 1,3-bis(hexafluoro-2-hydroxypropyl) benzene diglycidyl ether (3.00 g, 5.74 mmol) and methacrylic acid (0.99 g, 11.49 mmol) were combined with triphenylantimony (0.04 g) and 2,6-di-tert-butyl-4-methylphenol (BHT, 1.2 mg). Then the reaction mixture was sealed in a screw-capped vial and placed in an oil bath at 100° C. with stirring for 20 h. The crude product was dissolved in dichloromethane (10 mL) and extracted twice with a dilute aqueous sodium bicarbonate solution. the organic layer was dried over sodium sulfate and filtered. The solvent was removed from the filtrate under reduced pressure to provide the diol dimethacrylate as a very viscous colorless liquid in 92% yield.

Alternatively, α,α,α',α'-tetrakis(trifluoro-methyl-1,3-benzene-dimethanol (20.44 g, 49.8 mmol) was added to glycidyl methacrylate (14.17 g, 99.6 mmol), N,N-dimethylbenzylamine (0.34 g, 2.48 mmol) and 2,6-di-tert-butyl-4-methylphenol (BHT, 0.04 g). The neat mixture was sealed in a stopped flask and heated at 80° C. with stirring for 6 h. The reaction mixture was dissolved in dichloromethane (60 mL) and extracted twice with dilute aqueous hydrochloric acid. The organic layer was dried over sodium sulfate, decanted and the solvent evaporated under reduced pressure to give the viscous diol dimethacrylate product 9a as a near colorless liquid in 89% yield.

The diol dimethacrylate intermediate 9a (9.58 g, 8,61 mmol), an aliphatic diisocyanate (DDI 1410, Henkel Co., 5,17 g, 8.61 mmol) and dibutyltin dilaurate (0.15 g) were dissolved in toluene (75 mL). The reaction mixture was stirred under argon at room temperature for 40 h. The desired oligomeric multifunctional monomer 10a was isolated by precipitation from methanol (350 mL) followed by evaporation of the residual solvent under reduced pressure. The viscous, pale yellow product, was obtained in 86% overall yield.

Example 8
Synthesis of 10b 1,3-Bis(hexafluoro-2-hydroxypropyl)-5-perfluorooctyl benzene diglycidyl ether (13.00 g, 13.82 mmol) was combined with methacrylic acid (2.38 g, 27.65 mmol) and triphenyl antimony (0.15 g) as catalyst. 2,6-Di-tert-butyl-4-methylphenol (BHT, 4.6 mg) was added as polymerization inhibitor and the neat reaction mixture was stirred in an oil bath at 100° C. under argon for 20 h. In the second step, the clear viscous diol dimethacrylate intermediate (9.58 g, 8,61 mmol), an aliphatic diisocyanate (DDI 1410, Henkel Co., 5.17 g, 8.61 mmol) and dibutyltin dilaurate (0.15 g) were dissolved in toluene (75 mL). The reaction mixture was stirred under argon at room temperature for 40 h. The desired oligomeric multifunctional monomer 10b was isolated by precipitation from methanol (350 mL) followed by evaporation of the residual solvent under reduced pressure. The viscous, pale yellow product, was obtained in 86% overall yield.

Example 9
Synthesis of 12

Glycidyl methacrylate (18.00 g, 0.126 mol) and hexafluoro-2-propanol 42.60 g, 0.252 mol) were combined with N,N-dimethylbenzylamine (1.36 g, 0.01 mol) and heated at 65° C. for 24 hours. Excess hexafluoro-2-propanol was removed under reduced pressure to leave the product as a colorless, viscous liquid. A portion of the resulting hydroxy-substituted fluorinated methacrylate intermediate (16.34 g, 0.0527 mol) was diluted with toluene (20 mL) and combined with m-tetramethylxylene diisocyanate (6.40 g, 0.026 mol). The mixture was kept at 50° C. for 2 days under $N_2$ while monitoring the disappearance of the isocyanate peak at 2267 $cm^{-1}$ in the FT-IR spectra of aliquot samples. After the reaction was complete, toluene was removed under reduced pressure and a pale yellow, viscous product was obtained. GPC analysis of the oligomeric product provided polystyrene equivalent molecular weight peaks at 865.

Example 10
Synthesis of 13

The diol dimethacrylate intermediate 9a (2.10 g, 3.02 mmol) was combined with 2-isocyanatoethyl methacrylate (0.98 g, 6.3 mmol) and dibutyltin dilaurate (10 mg) in toluene 20 mL). The initially heterogeneous reaction mixture becomes a clear solution after 16 h at room temperature under argon. The solvent was removed under reduced pressure to leave the tetramethacrylate product 13 as a near colorless, slightly viscous liquid in quantitative yield. Product 13 has Formula 13.

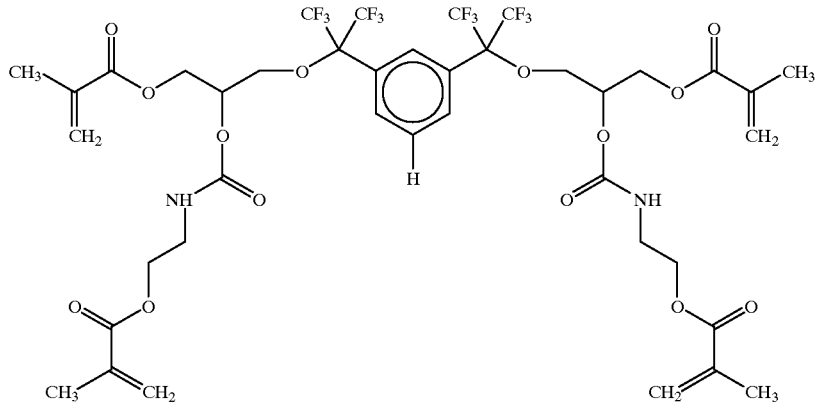

Properties of composites (made as described below) based on the above fluorinated monomers are disclosed in Table I.

The prepolymers of these examples have the capability to contain high percentages of fluorine by substitution at the pendent group Y (Formulas VII and/or XI) consistent with teachings of Griffith, J. R., *Chemtech*, 1982, 12, 290. The fluorine percentages of oligomers M-1, M-2, and M-3 of are 42.7, 50.7, and 52.4%, respectively.

B. Preparation of Composites

1. Silanization of Glass or Quartz Filler

A 100 g quantity of either glass (# 7724, Corning Glass Works; average particle size: 40 μm) or amorphous fused quartz (Fluka; average particle size: 25 tm) was added to 300 mL of cyclohexane in a 500 mL flask. Composites can be made with fillers of various particle sizes about 0.02 to 20 μm. A silane coupling agent (3-methacryloxypropyltrimethoxylsilane: 0.7 mass % by filler) and as catalyst (propylamine:2 mass % by filler) were added to silanize the surface of the glass (or quartz) filler. The flask was rotated on the rotary evaporator for 30 min at room temperature to allow complete mixing. The flask was then rotated with heating at 90° C. for 1 hour. A modest vacuum was then applied to evaporate the cyclohexane. Any unbound silane coupling agent and the amine catalyst were removed from the filler by washing with additional cyclohexane followed by filtration. The silanized filler was dried under vacuum (6 KPa) in an oven at 90° C. for 1 hour and then at room temperature for 12 hours.

2. Formulation of Resins and Composites

To evaluate their potential as components of dental resin formulations, the various highly fluorinated monomers (42–52 wt % fluorine) were mixed with 1,10-decamethylene glycol dimethacrylate (DMDM, Esschem Co.) a diluent comonomer used to control viscosity of the resins as follows. The refractive indices of the fluoromonomers M-1, M-2 and M-3, synthesized by the procedures described above, were measured. These monomers were then mixed with diluent copolymer, 1,10-decamethylene glycol dimethacrylate (DMDM: Esschem Co.) to provide resins with adequate viscosities. The proportion of diluent used with each fluorinated monomer was selected such that resins with good handling properties were obtained. Refractive indices of these mixtures of resins with DMDM were also measured.

A visible light photoinitiator system consisting of camphorquinone (CQ: Aldrich Chem. Co., mass fraction of 0.2%) and ethyl p-ethylaminobenzoate (also known as 4-N, N-dimethylaminobenzoate; DMAB) (Aldrich Chem. Co., mass fraction of 0.8%) was added to each resin formulation. Atrace amount of a separate photoinitiator (CGI-1700: CIBA-GEIGY Co.) was also added, and then completely mixed. The polymerization shrinkage of these unfilled resins was measured with a mercury dilatometer 10 shown in FIG. 1, by a procedure described in Patel, M. P.; Braden, M.; Davy, K. W. M. *Biomaterials* 1987, 8, 53; as well as Kinkelaar, M. ; Wang, B.; Lee, L. *J. Polymer* 1994, 35 (14), 301 1. As shown by FIG. 1, the mercury dilatometer 10 contains mercury 16 topped by a teflon float 14. The float 14 is attached to a linear variable displacement transducer (LVDT). The mercury dilatometer 10 measures polymerization shrinkage of an activated resin sample 18 placed on a quartz plate 20 and photocured using a visible light from a light device 22. The mercury dilatometer also includes a thermistor 24 for measuring temperature changes. A computer 26 is in communication with the thermistor 24, the light device 22 and the LVDT 12

Photocurable composite pastes were formulated by the addition of either silanized glass or amorphous quartz particulate filler to the resin mixtures. In the examples, dental material was cured by visible light, but the photoinitiator can be varied for UV cure or reduction-oxidation or thermal polymerization without light. The powder-liquid mixing ratios used to prepare the composite pastes are listed in Table I.

TABLE 1

Composition of Composites Based on Fluorinated Monomers

| Example | Monomer | DMDM (mass %) | Filler:resin (mass ratio) Glass | Filler:resin (mass ratio) Quartz | Fluorine (mass %) monomer/resin | RI for M*/(M* + DMDM) monomer/resin | Unfilled Resin density g/cm³ | Polymerization shrinkage of unfilled resins, % |
|---|---|---|---|---|---|---|---|---|
| 1 | 3a | 21.0 | 3.9 | 2.0 | 29.9/23.6 | 1.4680/1.4655 | 1.2684 | 4.14 |
| 2 | 3b | 18.9 | 3.1 | 2.0 | 22.0/17.8 | 1.4905/1.4845 | 1.3416 | 5.57 |
| 3 | 6 | 26.8 | 4.4 | 2.0 | 35.6/26.0 | 1.4690/1.4635 | 1.0447 | 6.02 |
| 4 | 8a (M-1) | 19.6 | 2.0 | 2.0 | 42.7/34.3 | 1.4340/1.4400 | 1.2855 | 3.56 |
| 4 | 8b (M-2) | 14.4 | 3.0 | 2.2 | 50.7/43.4 | 1.4150/1.4235 | 1.4480 | 3.38 |
| 5 | 8c (M-3) | 13.0 | 3.6 | 2.5 | 52.4/45.6 | 1.4125/1.4223 | 1.5087 | 4.06 |
| 7 | 10a | 47.0 | — | 2.8 | 17.8/9.4 | N/A/1.4543 | 1.16 | 8.19 |
| 8 | 10b | 33.0 | — | 2.8 | 32.4/21.7 | 1.4428/1.4504 | 1.20 | 7.81 |
| 9 | 12 | 13.0 | 4.0 | 2.0 | 27.2/23.7 | 1.4489/1.4495 | 1.1257 | 4.51 |
| 10 | 13 | 15.0 | — | 2.3 | 22.7/19.3 | N/A/1.4631 | 1.30 | 5.89 |

DMDM = 1,10-decamethylene glycol dimethacrylate
Composites include Glass or Quartz
RI (Refractive Index) measurements at 25° C.
M*: fluorooligomer
N/A: not available The composite pastes were then placed in a desiccator under vacuum for 12 hours to remove air incorporated during the mixing process. Specimens of the filled and unfilled resins were prepared in metallic molds clamped between mylar sheets and glass microscope slides. The specimens were then photocured by illumination with a 470 nm (λmax) visible light for 1 minute per side using a TRIAD 2000 curing device (Dentsply International, Inc., York, Pa.). After the photocuring, the composite samples were ejected from the molds and polished on silicon carbide abrasive paper (400 grit) using a HANDIMET GRINDER (Buehler Ltd. Evanston, Ill.) to get both flat surfaces and smooth edges. Photocured composites were then immersed in distilled water and placed in an oven at 37° C. for 2 days to allow the post-cure polymerization process to proceed prior to testing.

The evaluation of the fluorinated monomers and oligomers for use in dental resin applications required the addition of an appropriate amount of a diluent comonomer to each to control the overall viscosity of the resulting resins. The reactive diluent comonomer used was 1,10-decamethylene glycol dimethacrylate (DMDM), which offers good compatibility with a wide range of hydrophobic fluorinated monomers, whereas the more hydrophilic monomer TEGDMA was prone to phase separation in fluorinated resins either before or during polymerization. After omitting the resin based on the bromine-containing oligomer 3b, there is a clear trend (squared* linear regression correlation coefficient $r^2$=0.82) among the remaining fluorinated oligomers to require less diluent comonomer in resin formulation as the percentage of fluorine increases. The amount of diluent necessary to provide a workable resin viscosity is important since it influences the overall percentage of fluorine in the individual resins (Table 1). In general, minimum amounts of diluent are also preferred since relatively low molecular weight monomers contribute significant polymerization shrinkage. The two fluorinated monomers 12 and 13 require significantly less diluent than the fluorinated oligomers of comparable fluorine content. To complete the resin formulation, a visible light photoinitiator system consisting of camphorquinone (CQ) and ethyl 4-N,N-dimethylaminobenzoate (EDMAB) was added to each resin.

The refractive indices of both the monomers and their corresponding resins show a negative correlation with the fluorine content of the monomer and resin, respectively ($r^2$=0.83 and $r^2$=0.63, Table 1). The fluorinated resins range in refractive index from approximately 1.41 to 1.48. For comparison, a conventional dental resin, such as Bis-GMA/TEGDMA (7:3 mass ratio), has a refractive index of 1.5218 (22.5° C.). The bromine-containing oligomer 3b was included here to study the practicality of higher refractive index fluorinated resins that may allow more choice in the selection of fillers to be incorporated into fluorinated composite formulations. In general, it is desirable to have a relatively good match between the refractive index of the resin and filler to allow good light transmission for photopolymerization and to achieve a translucent polymeric composite that has an appearance similar to natural tooth structure.

The degree of conversion of thin films of the photocured unfilled fluorinated resins was determined by measuring the quantities of unreacted methacrylate groups remaining in the polymers using an infrared (FT-IR, Magna 550, Nicolet) spectroscopy technique. The ambient temperature photopolymerization conversion efficiency of a conventional Bis-GMA/TEGDMA resin (3:1 mas ratio) is in the range of 55% to 65%. Ideally, dental polymers would combine a high degrees of conversion, which improves mechanical properties and long-term stability, with low levels of polymerization shrinkage. The cyclopolymerizable oligomers considered here offer one method to attempt to satisfy these apparently contradictory goals. Likewise, monomers and oligomers designed with relatively low reactive group densities should also provide low shrinkage polymers. The degree of conversion of selected fluorinated resins was in the range of 70% to 80%. Part of the reason for the high conversion levels obtained with the fluorinated resins is likely a result of the lower cohesive energy of fluoropolymers. Since the typical ambient photopolymerization of dental resins and composites is limited by vitrification as the polymeric glass transition temperature ($T_g$) reaches the cure temperature, it is reasonable to expect higher conversion in fluorinated resins that start with a lower monomeric $t_g$ than comparable hydrocarbon resins.

The water contact angle, flexural strength (transverse strength), water uptake, and contact angle of these filled composites were measured and the results are listed in Tables II and III.

Physical properties of the photocured composites, including refractive index, water contact angle, transverse strength (TS), water uptake, by procedures described in Tillman, N., Ulman, A., Schildkraut, J. S., Penner, T. L., *J. Am. Chem. Soc.* 1988, 110, 6136.

TABLE II

Physical Properties of Resins and Composites based on Fluoromonomers

| Example | Resin/Filler | Flexural strength, MPa | Water contact angle, deg | Equilibrium water uptake, mass fraction |
|---|---|---|---|---|
| 1Q | 3a/Q | 64.7 (5.1) | 86.0 | 0.72 |
| 1G | 3a/G | 73.9 (8.7) | 85.5 | 0.54 |
| 2Q | 3b/Q | 73.9 (8.7) | 84.5 | 0.52 |
| 2G | 3b/G | 75.3 (7.6) | 85.0 | 0.28 |
| 3Q | 6/Q | 112.3 (12*) | 82.0 | 1.29 |
| 3G | 6/G | 81.3 (7*) | 80.0 | 0.73 |
| 4Q | 8a/Q (M-1Q) | 119.6 (6.8) | 88.0 | 0.23 |
| 4G | 8a/G (M-1G) | 108.9 (4.4) | 86.0 | 0.13 |
| 5Q | 8b/Q (M-2Q) | 82.6 (7.7) | 85.0 | 0.13 |
| 5G | 8b/G (M-26) | 92.8 (3.5) | 86.0 | 0.11 |
| 6Q | 8c/Q (M-3Q) | 70.7 (8.9) | 84.0 | 0.11 |
| 6G | 8c/G (M-3G) | 77.6 (1.0) | 89.0 | 0.15 |
| 7Q | 10a/Q | 118.1 (15) | 73.5 | 0.35 |
| 8Q | 10b/Q | 99.4 (11) |  | 0.19 |
| 9Q | 12/Q | 75.1 (6) | 84.0 | 0.50 |
| 9G | 12/G | 75.4 (2) | 82.0 | 0.28 |
| 10Q | 13/Q | 138.4 (12) | 70.0 | 0.63 |

TABLE III

Water Contact Angle Measurements on Resins and Composites Cured in the Absence or Presence of Air

| Resin | Fluorine in resin (mass fraction) | Filler content (mass fraction) | Contact angle, deg Mylar | Contact angle, deg Air | % change |
|---|---|---|---|---|---|
| EBPAD/DMDM | 0 | 0 | 75.7 | 68.4 | −9.6 |
| EBPAD/DMDM | 0 | 0.80 | 75.5 | 65.1 | −13.8 |
| 3a/DMDM | 23.6 | 0 | 83.8 | 63.8 | −23.9 |
| 3a/DMDM | 23.6 | 0.67 | 82.0 | 64.8 | −21.0 |
| 3b/DMDM | 17.8 | 0 | 82.0 | 62.3 | −24.0 |
| 3b/DMDM | 17.8 | 0.67 | 82.1 | 66.8 | −18.6 |
| 10a/DMDM | 9.4 | 0 | 76.9 | 61.4 | −20.2 |
| 10a/DMDM | 9.4 | 0.74 | 76.7 | 67.5 | −12.0 |
| 10b/DMDM | 21.7 | 0 | 80.9 | 66.4 | −17.9 |
| 10b/DMDM | 21.7 | 0.74 | 80.5 | 64.1 | −20.4 |

Density of filled resin is listed in Table IV.

TABLE IV

Density of Filled Resins

| Example | Sample | Den (g/cm$^3$) filled resins |
|---|---|---|
| 4Q | 8a/Q (M-1Q) | 1.9047 |
| 4G | 8a/G (M-1G) | 2.3016 |
| 5Q | 8b/Q (M-2Q) | 1.9714 |
| 5G | 8b/G (M-2G) | 2.4411 |

TABLE IV-continued

Density of Filled Resins

| Example | Sample | Den (g/cm³) filled resins |
|---|---|---|
| 6Q | 8c/Q (M-3Q) | 2.4727 |
| 6G | 8c/G (M-3G) | 2.7218 |

RI: refractive index, Den: density measurements, PS: volumetric polymerization shrinkage measurements.

The photocure of dental resins resulted in the formation of highly crosslinked, vitrified polymers that contain significant residual stresses due to polymerization shrinkage. These stresses can cause microcrack and void formation within the resin, debonding at the resin-filler interface, and marginal gap formation between the restoration and tooth substrate. Excessive polymerization shrinkage is one of the most serious problems related to the clinical application of dental resins and composites. In this evaluation, the polymerization shrinkage of the experimental fluorinated resins was measured using a mercury-filled dilatometer. This device provides quantitative dynamic measurements of the photo-induced polymerization shrinkage. A schematic diagram of the dilatometer is shown in FIG. 1. The simultaneous measurement of the mercury height and temperature allows thermal effects, such as the energy input from the visible light source and the resulting polymerization exotherm, to be separated from the continuous shrinkage measurement.

The volumetric shrinkage of a visible light photocured dental resin composed of Bis-GMA/TEGDMA (7:3 mass ratio) measured at 1 h was 7.96%. This result obtained with the mercury dilatometer is somewhat larger than the 6.95% volumetric contraction calculated for an identical resin photocured in a linear shrinkage measurement device. Differences in irradiation intensity could account for these differences. In FIG. 5, the percent volume contraction for the Bis-GMA/TEGDMA resin is plotted as a function of time during the photopolymerization. The shrinkage profile shows the volumetric change over the first 60 minutes as well as an expanded view of the first 30 seconds. The difference between the apparent shrinkage of 5.73% at 60 min and the reported value of 7.96% results from the need to compensate for a small amount of microfine silica filler (OX-50, Deguessa) added to the resin to decrease flow of the sample in the dilatometer prior to irradiation. Based on this same measurement technique, the polymerization shrinkages of the fluorinated resins based on 3a, 3b and 6 were calculated to be 4.14, 5.57 and 6.02%, respectively (Table I and FIGS. 4a–4j). Thus, the shrinkage of these cyclopolymerizable resins is significantly less than that of the Bis-GMA/TEGDMA material.

The polymerization shrinkages of activated resins based on 8a (M-1), 8b (M-2), and 8c (M-3) were calculated as 3.558, 3.376, and 4.065%, respectively. FIGS. 6a–6d show shrinkages of various samples versus time. Comparing these lower polymerization shrinkages to that of Bis-GMA (7.2%) by procedures of Venhoven, B. A. M., DeGee, A. J., Davidson, C. L., *Biomaterials* 1993, 14(11), 871; Stansbury, J. W., Antonucci, J. M., *Dent. Mater.* 1992, 8, 270; and Venz, S., Dickens, B., J. *Biomed. Mater. Res.* 1991, 25, 1231, shows the fluorinated monomers of the present invention result in dental polymers having lower volume shrinkage.

Thus, the polymerization shrinkage values obtained with resins based on the fluoroligomers 8a, 8b and 8c are measured in a range of 3% to 4%, which is less than half the Bis-GMA/TEGDMA contraction. The combination of the inert spacer units within the oligomer and the relatively rigid backbone structure are the likely reasons for the extremely low polymerization shrinkage values obtained with these three resins. The resin based on the fluorinated urethane dimethacrylate 12 also provides very low shrinkage. The shrinkage for the resin based on monomer 13 is surprisingly low considering its tetrafunctional structure. The significant reductions in polymerization shrinkage offered by these fluorinated resins compared with Bis-GMA/TEGDMA should ease the levels of residual stress and enhance the potential longevity of the polymerized resins and composites. Reduced shrinkage will also provide less change to the vulnerable restoration-tooth interface. The relatively high polymerization shrinkage values obtained with the resins based on monomers 10a and 10b points to high levels of conversion in these systems. Very high degrees of conversion have been observed previously with hydrocarbon resins based on the chain-extended oligomeric product of Bis-GMA and DDI.

An indication of the photopolymerization kinetics of the various resin systems is revealed in the dynamic shrinkage data. The initial slope of the photocure shrinkage curve of the Bis-GMANTEGDMA resin was calculated as 27.2 vol %/min. The early stage of the photopolymerization of each fluorinated resin is shown in the inset boxes of the shrinkage plots (FIGS. 2a–2j). the initial slopes of photocure curves of resins obtained from the fluorinated monomers and oligomers were calculated as 17.0, 19.0, 10.4, 17.4, 9.8, 9.5 and 15.3 vol. %/min, respectively. From this indirect measure of photopolymerization kinetics, it appears that among the fluorinated oligomers capable of cyclopolymerization, the bulky, branched oligomer 6 was the least reactive. The resin based on 6 also retained its initial linear cure rate significantly longer than any other resin in the study. Within the series of oligomers 8a–c, the unsubstituted oligomer 8a, even through higher in oligomeric molecular weight (by GPC compared with oligomers 8b and 8c), produced a resin with a much higher rate of cure than the $C_6$ and $C_8$ perfluoro-substituted homologs 8b and 8c, respectively. The resin containing the relatively small difunctional fluorinated monomer 12 provided no increase in the rate of photopolymerization compared with the oligomeric resins and was less reactive than the Bis-GMA/TEGDMA dimethacrylate resin. A decrease in mobility due to hydrogen bonding between urethane groups in 12 may be part of the explanation as to why this dimethacrylate-based resin was less reactive. In additional, more oxygen may be present in the resins with the higher fluorine contents. The dissolved oxygen would serve as a free radical inhibitor of the photopolymerization process.

In particular, FIGS. 2a–2j show the volume shrinkages as a function of time after the samples were irradiated. Slopes of volume shrinkages at an earlier photocuring stage for activated resins based on 8a (M-1), 8b (M-2), and 8c (M-3) were calculated as 17.40, 9.78, and 9.46, respectively. The activated resin based on M-1 shows a rapid volume shrinkage two times faster than those of resins based on M-2 and M-3. According to GPC results, a weight average molecular weight of M-1 was higher (Mw=17,175) than those of resins based on M-2 and M-3. Thus, the higher degree of polymerization would cause a rapid volume shrinkage of M-1. The degree of conversion obtained for the various multifunctional fluoroprepolymers described here was successfully increased to 70 to 80% as a result of the cyclopolymerization process and the lower cohesive energy inherent in fluoropolymers. The low values of polymerization shrinkage associated with all these novel fluorinated composites is another important criteria in judging their potential as prospective dental materials. Minimized polymerization shrinkage improves the clinical performance of composite restorations. While traditional dental resins produce volumetric shrinkages of 7 to 9%, some of the fluorinated resins of the present invention offer reductions of 50% or more. FIG. 5 shows the volume shrinkage for the Bis-GMA/TEGDMA resin.

Either amorphous quartz or sodium borosilicate glass particulate filers, which had been silanized with 3-methacryloxypropyltrimethoxysilane, were combined with the resins to prepare to the photocurable pastes (Table I). The quartz filler was used because it provides a reasonably good refractive index match ($n_D^{20}$=1.4585) with the various fluorinated resins. For the most part, the quartz filler loading level was fixed at a 2:1 mass ratio (filler to resin). The glass filler was included because of the radiopacity that results from its barium content. It is often desirable to have dental restorative materials that can be visualized by X-ray for the diagnostic purposes. The barium glass filler has a refractive index ($n_D^{20}$ ca. 1.55) that is substantially higher than that of any of the resins examined here, including the bromine-containing resin. However, the resin containing 3b did produce the most translucent glass-filled composite samples. For each fluorinated resin, the glass filler loading level was allowed to vary such that a composite paste with an easily handlable consistency was achieved. With the exception of the resin from 3b, which is more dense due to the bromine content, the densities of the fluorinated resins increased with the fluorine content.

In an examination of the hydrophobic nature of the fluorinated composites, water contact angle and water uptake were measured for photocured disks with the results listed in Table II. The static water contact angles measured on fluorocomposite disks were relatively high, especially when compared with that of a quartz-filled Bis-GMA/TEGDMA composite (68.6°). In general, there were only very weak correlations between either contact angle or water uptake and the percentage of fluorine present in the various resins. In all cases except one, the quartz-filled composites had greater water uptake than the corresponding glass-filled composites. However, this difference appears to be related to the level of filler loading rather than the filler type. The use of glass filler allowed the formulation of composites with significantly higher filler contents than could be achieved using quartz filler. When the water uptake data are normalized to account for the fraction of resin in each composite, there are only modest differences between quartz and glass filled materials. The type of filler in the composite had no influence on the contact angle. This would be expected since the composite surfaces tested were polymerized against mylar and would be rich in the resin phase. Different results might be anticipated if polished surfaces that exposed more of the filler particles were used for the contact angle measurements. The presence of hydrogen bonding urethane groups may be responsible for the relatively low water contact angles measured for the composites containing 10 and 13.

Figure 3A:
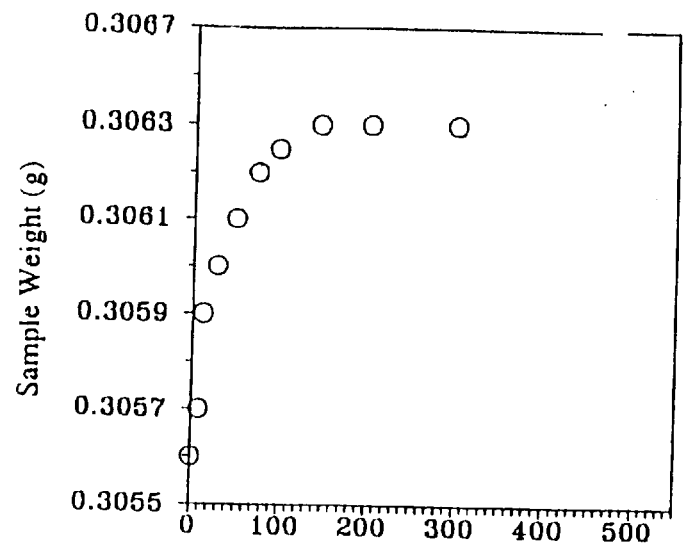
FIGS. 3a–3c are plots of water uptake percentages of fluorinated dental composites based on prepolymer samples.
Figure 3B:
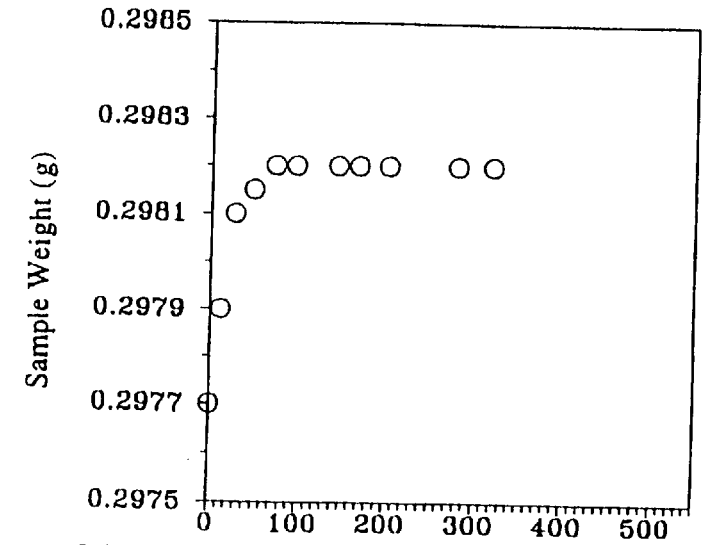
Figure 3C:
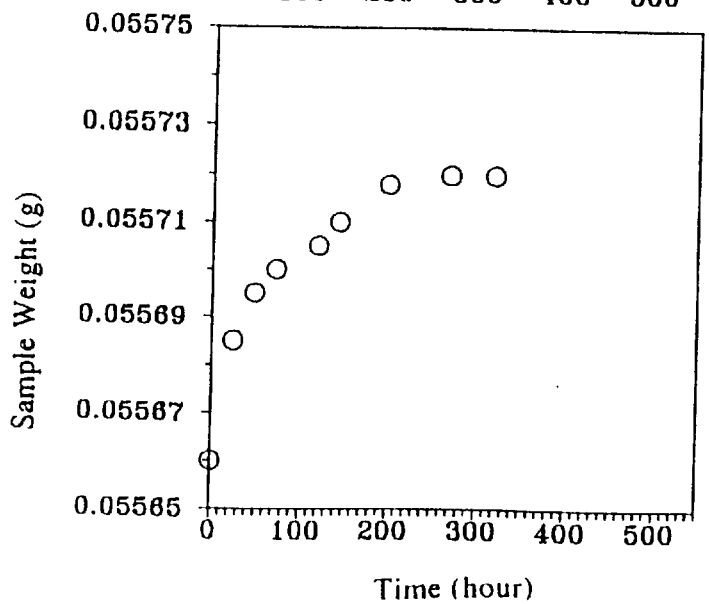
Figure 6A:
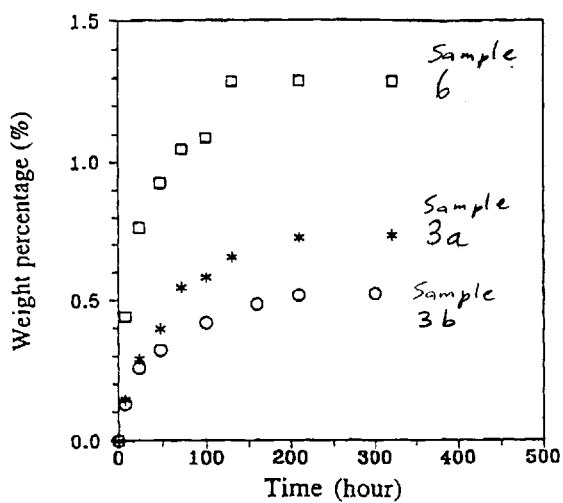
FIGS. 6a–6d plot water uptake weight percentage versus time.
Figure 6B:
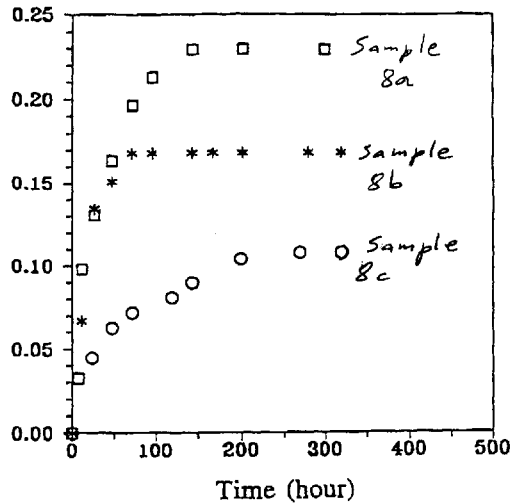
Figure 6C:
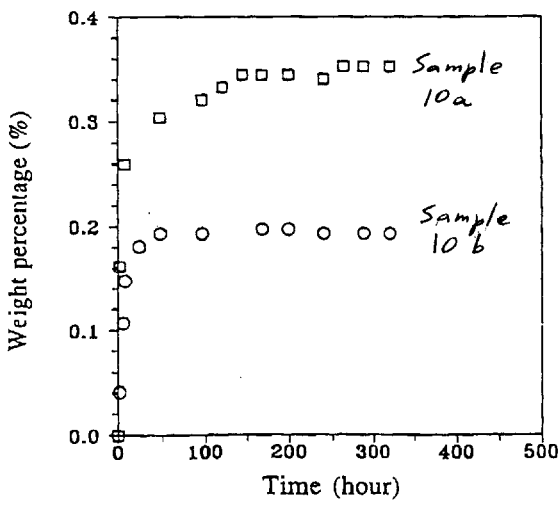
Figure 6D:
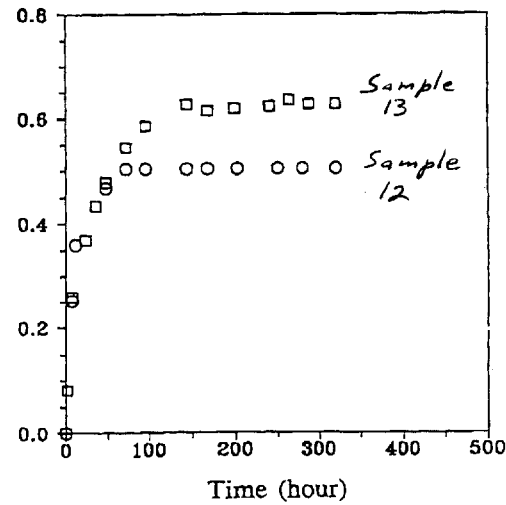

The equilibrium water uptake of the various fluorinated composites is shown in Table II. There does appear to be some correlation between the percentage of fluorine in a given resin and the water sorption of its corresponding composite material. The series of composites based on 8a–c, which have the highest levels of fluorine incorporated, produced the lowest levels of water uptake. Structural features other than the percentage of fluorine in these monomers also influence the amount of water uptake in a composite. The relatively high water sorption observed for materials based on oligomer 6 can be explained by the high concentration of hydroxyl groups in this oligomer. In contrast, the cyclopolymerizable bromine-substituted oligomers 3b provided relatively low water uptake as did monomers 10a and 10b even with their polar urethane functional groups. For comparison, the water uptake of a comparable quartz filled composite based on Bis-GMA/TEGDMA (7:3 mass ratio) was 1.22 mass percent. Therefore, most of the composites based on these fluorinated resins show a significant improvement in hydrophobicity over that characteristic of conventional dental composite materials. The water uptake into quartz filled composites as a function of immersion time is shown in FIGS. 3a–3c. The pattern of water uptake for the composites based on oligomers 3a, 3b and 8c is similar with a relatively gradual approach to an equilibrium value. This differs from the more rapid water uptake profiles for composites based on oligomers 8b, 10a, 10b and 12, which reach a plateau region in less than 100 hours of immersion.

FIG. 3 shows the water uptakes of the highly fluorinated dental composites. In the plots of water uptake measurements for composites based on M-1(8a), M-2(8b), and M-3(8c), the data points reached their maximum region within 100 hours. Water uptake % s based on the monomers were measured at very low values, 0.1–0.2 wt. %. Water uptake % of a composite based on Bis-GMA was reported as 3.8 wt % according to the following references Venhoven, B. A. M., DeGee, A. J., Davidson, C. L., *Biomaterials* 1993, 14(11), 871; Stansbury, J. W., Antonucci, J. M., *Dent. Mater.* 1992, 8, 270; and Venz, S. Dickens, B. J. *Biomed. Mater. Res.* 1991, 25, 1231.

Within the series of composites based on prepolymers M-1(8a), M-2(8b), and M-3(8c), the mechanical strength decreases with increasing fluorine content. However, all these materials and especially composites containing prepolymer M-1 (8a), demonstrated good strength properties. The enhanced mechanical strength observed with prepolymer M-1 (8a) was probably due to its very rigid regular backbone structure. The water uptake among this series of composites was extremely low.

The results of three-point bending flexural strength (FS) measurements for photocured bar specimens of the fluorinated composites are summarized in Table II. The stress-strain curves generated during testing to failure can be analyzed to obtain both the flexural strength and the flexural modulus of the composites. Representative individual plots of the transverse strength measurements of the fluorinated composites are shown in FIGS. 4a–4j.

Most commercial dental composites which have been used in dental applications show flexural strength of 90 MPa to 140 MPa. The flexural strength results of the prepared composites of the present invention show that there are several fluorinated monomer or oligomer structures that have potential as high strength materials. The composites based on 8a and 10a appear to offer the best combination of high mechanical strength and low water uptake. FIGS. 6a–6d show water uptake as a function of immersion time into quartz filled samples. The good strength of the fluorinated composites could likely be improved by the use of a silane coupling agent other than 3-methacryloxypropyltrimethoxysilane, that has better compatibility with the fluorinated resins. Preliminary results using a more hydrophobic coupling agent have demonstrated that significantly higher filler loading can be achieved in composites prepared with fluorinated resins. The incorporation of more filler should improve not only the mechanical strength of the fluorinated composites, but also further reduce polymerization shrinkage and water uptake.

In particular, FIGS. 4a–4j and Table II, show and list, respectively, the results of three-point bending flexural strength (FS) (transverse strength (TS)) measurements on the fluorocomposites. The three-point bending flexural strength (TS) measurements show excellent results. The high strength polymeric networks derived from (meth) acrylate resins with moderate to high organofluorine contents produced a high physical strength (70–120 MPa). In FIG. 4, two straight lines show the flexure modulus curve and the integration curve. The modulus of fluorocomposites based on 8a/Q (M-1), 8b/Q (M-2), and 8c/Q (M-3) and filled with quartz filler were measured as 11.5, 10.8, and 10.2 GPa, respectively.

A powdered glass-filled composite based on the Bis-GMNTEGDMA resin (1:4 resin-filler by mass) provides DTS and TS values of 50.5±1.3 MPa and 91.4±8.5 MPa, respectively, as reported by Hu, H. S. W., Griffith, J. R. *Polym. Prepr.* 1993, 34(1), 401; Guo, X. A. Hunter, A. D., Chen, J. J. *Polym. Sci.: Polym. Chem.* 1994, 32, 47; Jariwala, C. P., Mathias, L. J. Macromolecules 1993, 26, 5129. This improved TS of the resins of the present invention coupled with the strong, hydrophobic character of certain fluorinated composites examined here, make these materials excellent materials for dental restoratives with the potential for improved durability.

(2×diol); 0.0267 g amine (0.20 mmol) (2 mol % based on epoxy) (0.2–5.0 mol % may be used if desired).

The mixture was placed in a screw capped vial and the reaction occurred in the screw capped vial in an oil bath without stirring. There was a DURASEAL film over the viavunder the lid and the mixture was heated at 80° C. for 4 hours (typically temperatures of 80° C–100° C. could be employed). $^1$HNMR was checked in $CDCl_3$.

There were strong peaks at 2.6, 2.9 and 3.2 ppm. These appear to be the epoxy signals. The $CF_2$—H peak is present at about 5.7 ppm as a triplet. This peak looks significantly larger than the corresponding epoxy peaks. In addition, there is a doublet of doublets at about 3.9 ppm that corresponds to the $OCH_2CH$—$CH_2$ epoxy methylene group. New peaks are present at a 3.0, 3.7 and 4–4.3 ppm. These are related to the ring-opened product.

The vial was replaced in the 80° C. oil bath overnight.

$^1$HNMR of above reaction mixture shows further reaction at about 20 h/80° C. The epoxy related peaks designated above are reduced to about 25–30% and strong peaks at 3.7, 4.1 and 4.2 are present. The vial was resealed and put into oil bath with temperature increased to 95° C. The reaction mix viscosity is significantly higher after 20 hours at 80° C. then originally.

After 6 hours at 95° C., the $^1$HNMR was rerun and all the epoxy-related signals are gone. The fluorinated diol intermediate product is a viscous but mobile yellow liquid having the following Formula Int.

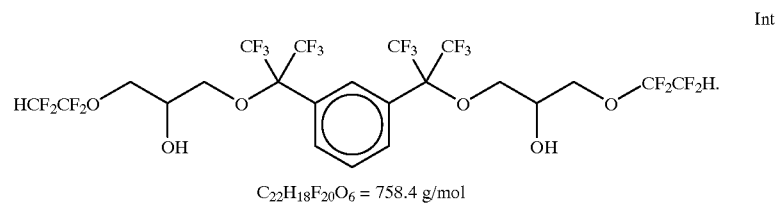

Int $C_{22}H_{18}F_{20}O_6 = 758.4$ g/mol

Example 10

Synthesis of a Compound of Formula IIId

A compound of Formula IIId was synthesized as follows:

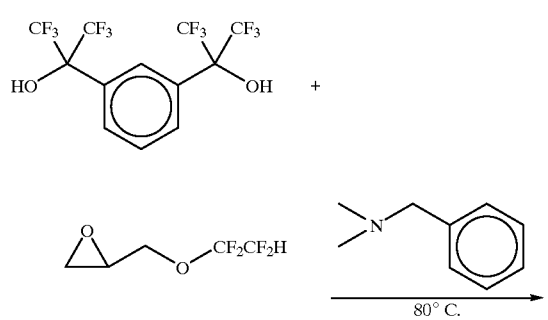

using the following amounts of ingredients: 2.0278 g diol (4.94 mmol); 1.7215 g fluorinated epoxy (9.89 mmol)

The crude reaction mixture was used without purification. From the initial reaction, which gave 4.94 mmol of the fluorinated diol intermediate, this intermediate was combined with two equivalents of methacryloyl chloride and triethylamine in dichloromethane in the following amounts:

Fluorinated diol 4.94 mmol methacryloyl chloride 9.88 mmol=1.0328 g triethylamine 10.00 mmol=1.0119 g The fluorinated diol was dissolved into about 8 mL $CH_2Cl_2$. The triethylamine was added. The flask was connected to a dry argon purge and cooled in an ice bath to about 5° C. The methacryloyl chloride was diluted with 2 mL $CH_2Cl_2$ and added to the stirred solution dropwise. The reaction then proceeded at room temperature overnight (0° C.–50° C. range).

The above reaction was extracted with 10 mL of dilute aq. HCl followed by a second extraction with dilute aq. $NaHCO_3$ to recover a product of Formula Q. The dichloromethane layer was collected and concentrated under reduced pressure to leave a pale yellow moderately viscous liquid. IR shows no OH remaining.

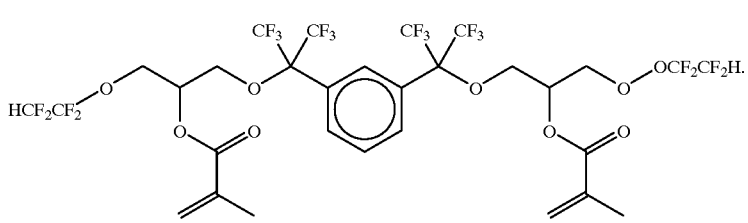

While only certain preferred embodiments of this invention have been shown and described by way of illustration, many modifications will occur to those skilled in the art and it is, therefore, desired that it be understood that it is intended herein to cover all such modifications that fall within the true spirit and scope of this invention.

We claim:

1. A multifunctional moiety with pendant methacrylate groups selected from the group consisting of moieties of Formulas II, IIIa, IIIb, IIIc, IIId and IV:

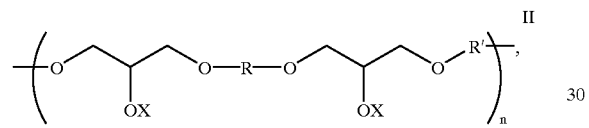

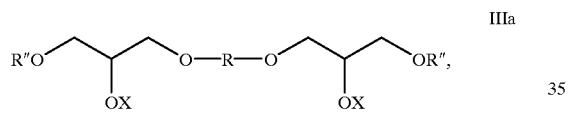

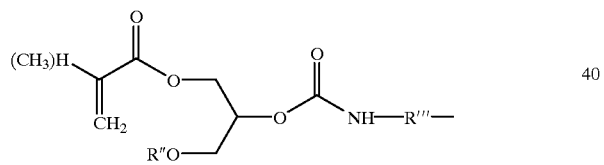

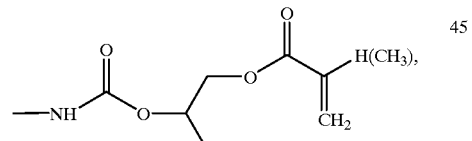

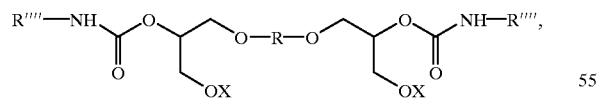

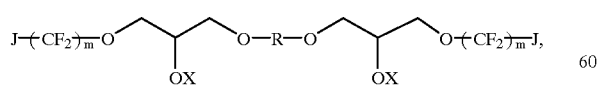

wherein J is a member of the group consisting of H and F, and m is an integer from 1 to 12,

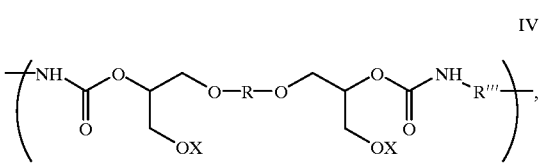

in Formulas II and IV, n ranges from 2 to sufficient to provide prepolymers having a weight average molecular weight of about 5000–30,000 and the end groups (not shown) are selected from the group consisting of acrylate, methacrylate, isocyanato (methacrylics, fumarates and maleates;

in Formulas II, IIIa, IIIb, IIIc, IIId and IV, X is selected from the group consisting of moieties V and VI:

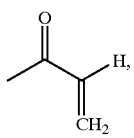

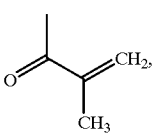

R and R' are selected from the group consisting of moieties VII, VIII, IX, and X:

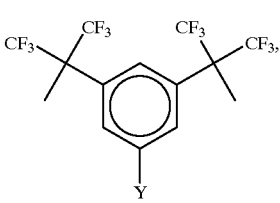

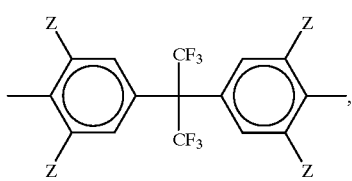

wherein Z is selected from the group consisting of H and Br, $$-CH_2-(CF_2)_x-CH_2- \qquad IX,$$

wherein x is an integer from 1 to 12, and

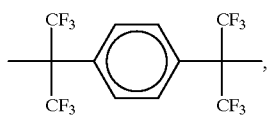 X group Y of moiety VII is selected from the group consisting of —H and —(CF$_2$)$_x$F, wherein x is an integer from 1 to 12, R″ is selected from the group consisting of moieties XV, XVI, and XVII:

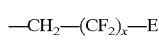 XV, wherein x is an integer from 1 to 16 and E is H or F,

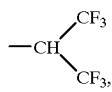 XVI

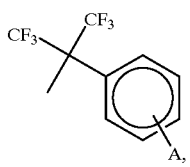 XXVII wherein A is H or —CH$_3$,

R′″ is selected from the group consisting of moieties XVIII, XIX, XX, XXa, XXI, XXII, XXIIa, and XXIIb:

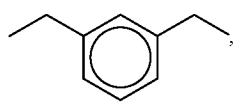 XVIII

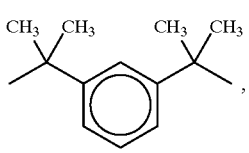 XIX

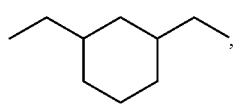 XX

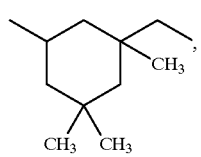 XXa

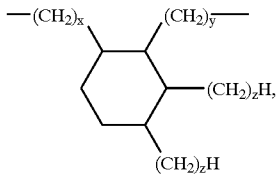 XXI

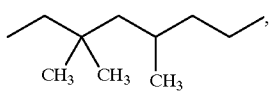 XXII

 XXIIa wherein x is an integer from 1 to 12,

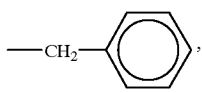 XXIIb the polymerizable fluorinated acrylate and methacrylate prepolymers, moieties II, III, and IV contain 15 to 65% by mass fluorine; moieties II and IV may have weight average molecular weights from about 5000 up to about 30,000, R″″ is selected from the group consisting of:

 IIIe, wherein m is an integer from 1 to 18,

 IIIf

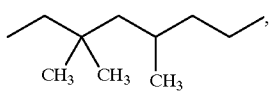 IIIg and

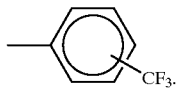 IIIh

2. The moiety of claim 1, wherein the moiety of claim 1, wherein the moiety has Formula II and R has Formula VII and R′ has Formula IX.

3. The moiety of claim 1, wherein the moiety has Formula IIIa.

4. The moiety of claim 1, wherein the moiety has Formula IIIb.

5. The moiety of claim 1, wherein the moiety has Formula IIIc.

6. The moiety of claim 1, wherein the moiety has Formula IIId.

7. The moiety of claim 1, wherein the moiety has Formula IV.

8. A dental composite comprising a mixture of a filler and a high strength polymeric network derived from resins comprising at least one cured moiety selected from the group consisting of Formula II, IIIa, IIIb, IIIC, IIId and IV of claim 1.

9. A process for synthesizing the moieties of Formula II of claim 1, comprising the steps of:

reacting a diglycidyl ether of Formula XXIII

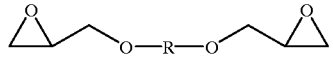

XXIII with a hydroxy-containing compound of Formula XXIV

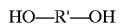    XXIV;

at reaction conditions comprising a temperature within the range of about 90° C. to about 120° C. for a time from about 6 hours to about 30 hours to produce a reaction product, the reaction product is combined with at least one member of the group consisting of chloro(acrylate), chloro(meth)acrylate, and isocyanato (meth)acrylics at room temperature in the presence of a tertiary amine under a nitrogen atmosphere to produce a reaction product; and reacting the reaction product with a methacrylate monomer or acrylate monomer to synthesize the prepolymer of Formula II;

wherein the groups R, R', X and Y have the same meanings as in the Formula II.

10. The process of claim 9, wherein R and R' have Formula VII.

11. A process for synthesizing the moieties of Formula IIIa of claim 1, comprising the steps of:

reacting a diglycidyl ether of Formula XXIII

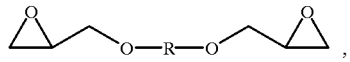

XXIII with a hydroxy-containing compound of Formula XXVI

    XXVI, at reaction conditions comprising a temperature within the range of about 90° C. to about 120° C. for a time from about 6 hours to about 30 hours to produce a reaction product; and reacting the reaction product with a methacrylate monomer or acrylate monomer to synthesize the prepolymer of Formula III;

wherein the groups R, R' and X have the same meanings as in the Formula IIIa.

12. A process for synthesizing the moieties of Formula IIIb of claim 1, comprising the steps of:

reacting an ether of Formula XXVA

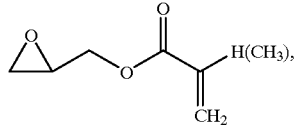

XXVa with a hydroxy-containing compound of Formula XXVI

    XXVI at reaction conditions comprising a temperature within the range of about 90° C. to about 120° C. for a time from about 6 hours to about 30 hours to produce a reaction product of Formula XXVb:

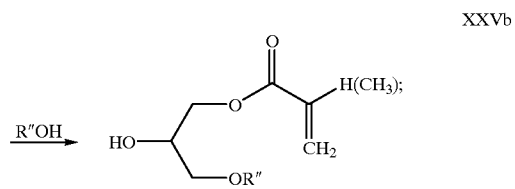

XXVb and reacting the reaction product with a diisocyanate of formula OCN—R'''—NCO at a temperature of from about 20° C. to about 60° C. and for a time of about 2 to about 30 hours to synthesize the prepolymer of Formula IIIb;

wherein the groups R'' and R''', have the same meanings as in the Formula IIIb.

13. A process for synthesizing the moieties of Formula IIIc of claim 1, comprising the steps of:

reacting a hydroxy containing compound of Formula XXVIIa

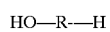    XXVIIa, with a glycidal ether compound of Formula XXVIIIa

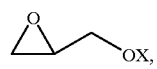

XXVIIIa at reaction conditions comprising a temperature within the range of about 60° C. to about 120° C. for a time from about 6 hours to about 30 hours to produce a compound of Formula XXIX,

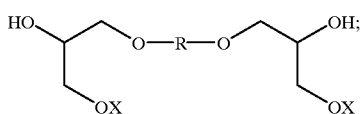

XXIX reacting the compound of Formula XXIX with an isocyanate of Formula XXXa

    XXXa, at a temperature of about 20° C. to about 60° C. and for a time of about 2 to 30 hours to produce the prepolymer of Formula IIIc;

wherein the groups R and R'''' and X have the same meanings as in the Formula IIIc.

14. A process for synthesizing the moieties of Formula IIId of claim 1, comprising the steps of:

reacting hydroxy-containing compound of Formula XXVIa

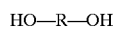    XXVIIa with a glycidyl ether-container compound of Formula XXIV;

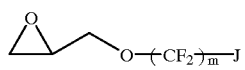
XXIVa wherein moiety J is selected from the group consisting of H and F and m is an integer from 1 to 12, in the presence of an amine compound comprising a moiety of Formula XXIVb

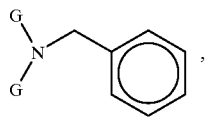
XXIVb wherein the amine compound is present in an amount of 0.2 to 5.0 mole % based on total weight of the compound of Formula XXIVa and each G is independently H, $CH_3$ or $C_2$–$C_{12}$ alkyl at reaction conditions comprising a temperature within the range of about 60° C. to about 120° C. for a time from about 6 hours to about 30 hours to produce a compound of Formula XXIXd,

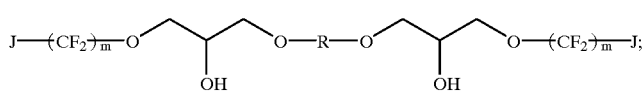
XXIXd and reacting the compound of Formula XXIXd with a chloromethacrylate or chloroacrylate to synthesize the prepolymer of Formula IIId;

wherein J, m and R are defined as in Formula IIId.

15. A process for synthesizing the moieties of Formula IV of claim 1, comprising the steps of:

reacting a diglycidyl ether of Formula XXIII

XXIII

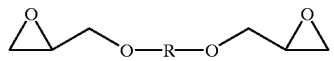

with a vinyl-containing carboxylic acid compound of formula XXVIII

HOX     XXVIII at reaction conditions comprising a temperature within the range of about 60° C. to about 120° C. for a time from about 6 hours to about 30 hours to produce a compound of Formula XXIX,

XXIX

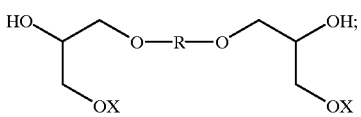

reacting the compound of Formula XXIX with a diisocyanate of Formula XXX

OCN—R'"—NCO     XXX at a temperature of about 20° C. to about 60° C. and for a time of about 2 to 30 hours to produce the prepolymer of Formula IV;

wherein the groups R, R'" and X have the same meanings as in the Formula IV.

16. A process for synthesizing the moieties of Formula IV of claim 1, comprising the steps of:

reacting a hydroxy-containing compound of Formula XXVIIa

HO—R—OH     XXVIIa with a glycidyl ether compound of Formula XXVIIa

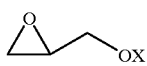
XXVIIIa at reaction conditions comprising a temperature within the range of about 60° C. to about 120° C. for a time from about 6 hours to about 30 hours to produce a compound of Formula XXIX,

XXIX

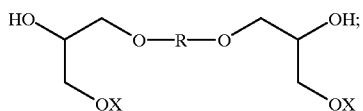

reacting the compound of Formula XXIX with a diisocyanate of Formula XXX

OCN—R'"—NCO     XXX at a temperature of about 20° C. to about 60° C. and for a time of about 2 to 30 hours to produce the prepolymer of Formula IV;

wherein the groups R, R'" and X have the same meanings as in the Formula IV.

17. A method of using the prepolymer of claim 1 comprising:

placing the prepolymer in a mouth of a patient and curing the prepolymer in the mouth of the patient by applying light to the prepolymer.

* * * * *